United States Patent [19]
Briles et al.

[11] Patent Number: 5,980,909
[45] Date of Patent: *Nov. 9, 1999

[54] EPITOPIC REGIONS OF PNEUMOCOCCAL SURFACE PROTEIN A

[75] Inventors: David E. Briles; Janet L. Yother; Larry S. McDaniel, all of Birmingham, Ala.

[73] Assignee: UAB Research Foundation, Birmingham, Ala.

[*] Notice: This patent is subject to a terminal disclaimer.

[21] Appl. No.: 08/319,795

[22] Filed: Oct. 7, 1994

Related U.S. Application Data

[63] Continuation-in-part of application No. 08/246,636, May 20, 1994, which is a continuation-in-part of application No. 08/048,896, Apr. 20, 1993, abandoned, which is a continuation-in-part of application No. 07/835,698, Feb. 12, 1992, abandoned, which is a continuation-in-part of application No. 07/656,773, Feb. 15, 1991, abandoned.

[51] Int. Cl.$^6$ .................................................. A61K 39/09
[52] U.S. Cl. ................................... 424/244.1; 424/190.1; 435/320.1; 530/350; 530/825
[58] Field of Search ........................ 435/320.1; 530/350, 530/825; 424/244.1, 190.1

[56] References Cited

PUBLICATIONS

McDaniel et al. Jan. 1991. Infection & Immunity 59(1): 222–228.
Talkington et al. Apr. 1991. Infection & Immunity 59(4): 1285–1289.
McDaniel et al. Abstract No. D–255. Abstracts of the 89$^{th}$ Annual Meeting of the Amer. Society for Microbiology. New Orleans, La. May 14–18 1989.

*Primary Examiner*—Christopher L. Chin
*Assistant Examiner*—Jennifer Graser
*Attorney, Agent, or Firm*—Frommer Lawerence & Haug LLP; William S. Frommer; Thomas J. Kowalski

[57] ABSTRACT

Regions of the PspA protein of the Rx1 strain of *Streptococcus pneumoniae* have been identified as containing protection-eliciting epitopes which are cross-reactive with PspAs of other *S. pneumoniae* strains and which is cross-protective. One region comprises the 68-amino acid sequence extending from amino acid residues 192 to 260 of the Rx1 PspA, another region comprises the C-terminal amino acid sequence extending from amino acid residues 293 to 588 of the Rx1 PspA, while a third region comprises the N-terminal amino acid sequence extending from amino acid residues 1 to 115 of the Rx1 PspA.

13 Claims, 7 Drawing Sheets

| | | | | | | | | | | | |
|---|---|---|---|---|---|---|---|---|---|---|---|
| 661 GAA glu | GCT ala | | 221 AAA lys | GCA ala | AAA lys | TTA leu | GAA glu | GAG glu | 691 AAA lys | AAA lys | ACT thr | GAA glu | GCC ala | AAA lys | CAA gln | AAA lys | GTG val |
| 721 GAT asp | GCT ala | | 241 GAA glu | GAA glu | GTC val | GCT ala | CCT pro | AAA lys | 751 ATC ile | GCT ala | TTG leu | GAA glu | AAT asn | CAA gln | GTT val | CAT his | AGA arg |
| 781 CTA leu | GAA glu | | 261 CAA gln | GAG glu | CTC leu | GCT ala | AAA lys | GAG glu | 811 ATT ile | GAA glu | TCA ser | CAT his | TAT tyr | GCT ala | AAA lys | GAA glu | GGT gly |
| 841 TTC phe | CCT pro | | 281 GCT ala | CCT pro | CTT leu | AAA lys | TCT ser | GAT asp | 871 GCG ala | TAC tyr | TCA ser | AAA lys | CTA leu | TCA ser | GAT asp | CTT leu | GAA glu |
| 901 CAG gln | AGT ser | | 301 GCT ala | GAT asp | AAG lys | ATT ile | CAA gln | GAT asp | 931 GCT ala | GAA glu | AAA lys | AAA lys | CTT leu | GAA glu | AAA lys | CAA gln | CTT leu |
| 961 TTA leu | GCT ala | | 321 AGT ser | GAA glu | GAA glu | AAT asn | GAG glu | GAC asp | 991 GCT ala | GLU glu | GCA ala | GAA glu | GGT gly | TTA leu | GAT asp | GAA glu | ACT thr |
| 1021 AAA lys | GCT ala | | 341 GCT ala | AAA lys | AAA lys | AAA lys | TTA leu | GAA glu | 1051 GAC asp | TAC tyr | CTT leu | GAA glu | AAG lys | CCA pro | AAA lys | GTT val | AAT asn |
| 1081 ATT ile | GCT ala | | 361 GCT ala | AAA lys | CCA pro | GAA glu | GCT ala | AAA lys | 1111 ACT thr | GAA glu | CCA pro | GCA ala | CCA pro | CCA pro | GAA glu | GAA glu | CAA gln |
| 1141 GAG glu | GAA glu | | 381 GAA glu | CCA pro | CCG pro | GCT ala | CCT pro | GCT ala | 1171 ACT thr | CCT pro | GCC ala | GAG glu | TAT tyr | GAT asp | AGA arg | GCT ala | GAA glu |
| 1201 CCA pro | AAA lys | | 401 CCA pro | TAT tyr | CAA gln | CAA gln | CCT pro | GCT ala | 1231 CCC pro | CCA pro | CCA pro | AAG lys | CAA gln | CCA pro | CGT arg | AGA arg | TCA ser |
| 1261 CAA gln | CCA pro | | 421 AAA lys | ACA thr | TTG leu | AAA lys | AAA lys | CAG gln | 1291 CAA gln | CAA gln | AAA lys | GAG glu | CAA gln | CCA pro | CCA pro | GCT ala | CCT pro |
| 1321 GCA ala | CCA pro | | 441 CCA pro | GGC gly | TGG trp | AAT asn | CAA gln | CAG gln | 1351 GGT gly | ATG met | TGG trp | TAC tyr | TTC phe | TAC tyr | AAT asn | GAT asp | GGT gly |

FIG. 1c

```
1381 /
     TCA
     ser
1441 /    461
     GCT  GCG  ACA  GGA  TGG  CTC  CAA  AAC  AAC        TGG  TAC  CTC  AAC· AGC  AAT  GGT
     ala  ala  thr  gly  trp  leu  gln  asn  asn  1411 trp  tyr  leu  asn  ser  asn  gly
1501 /    481                                      471                                    
     GCT  GCT  ACA  GGT  TGG  CTC  CAA  AAC  AAT  GGT TGG  TAC  CTC  AAC  GCT  AAC  GGC
     ala  ala  thr  gly  trp  leu  gln  asn  asn  gly trp  tyr  leu  asn  ala  asn  gly
          501                                      1471/     491
1561 /                                              TCA
     GCT  GCT  ACA  GGT  TGG  CTC  CAA  TAC  AAC  GGT ser  TAC  CTC  AAC  GCT  AAT  GGT
     ala  ala  thr  gly  trp  leu  gln  tyr  asn  gly 1531/ tyr  leu  asn  ala  asn  gly
          521                                      TGG       511
1621 /                                              trp
     GCT  GCT  ACA  GGT  TGG  GCT  CAA  AAA  AAC  GGT      TAT  TAC  CTC  AAC  GCT  AAC  GGC
     ala  ala  thr  gly  trp  ala  gln  lys  asn  gly TCA  tyr  tyr  leu  asn  ala  asn  gly
          541                                      ser  531
1681 /                                              1591/
     GCT  GCA  ACA  GGT  TGG  CTC  CAA  TAC  AAC  GGT TGG  TAC  TAC  CTC  AAC  GCT  AAT  GGT
     ala  ala  thr  gly  trp  leu  gln  tyr  asn  gly trp  tyr  tyr  leu  asn  ala  asn  gly
          561                                      TCA  551
1741 /                                              ser
     GCT  GCT  ACA  GGT  TGG  GCT  CAA  AAA  GTC  GGT 1651/ TAC  TAC  CTC  AAC  GCT  AAC  GGC
     ala  ala  thr  gly  trp  ala  gln  lys  val  gly TGG  tyr  tyr  leu  asn  ala  asn  gly
          581                                      trp  571
1801 /                                              
     GCT  GCT  ACA  GGT  TGG  CTC  CAA  TAC  AAC  GGT TCA  TAC  TAC  CTC  AAC  GCT  AAT  GGT
     ala  ala  thr  gly  trp  leu  gln  tyr  asn  gly ser  tyr  tyr  leu  asn  ala  asn  gly
          601                                      1711/ 591
1861-                                               TGG
     GCT  GCA  ACA  GGT  TGG  GCT  CAA  AAA  GAT  GGA trp  TAC  TAT  CTT  GAA  GCA  TCA  GGT
     ala  ala  thr  gly  trp  ala  gln  lys  asp  gly TCA  tyr  tyr  leu  glu  ala  ser  gly
          621                                      ser  611
1921 /                                              1771/
     GCT  AAA  GCA  AGC  CAA  TGG  TTC  AAA  GTA  TCA TGG  TGG  TAT  TAT  GCC  AAT  GGT  GAA
     ala  lys  ala  ser  gln  trp  phe  lys  val  ser trp  trp  tyr  tyr  ala  asn  gly  glu
          641                                      ACC  631
1981 /                                              thr
     GCT  CTT  GCA  GTC  AAC  ACA  ACT  AAA  GTA  GGC 1831/ GTC  ACA  TAA  TGA  GGT  AAC
     ala  leu  ala  val  asn  thr  thr  lys  val  gly GAT  val  thr  ***  ***  gly  asn
          661                                      asp  651
2041 /                                              1891/
     GCT  GCC  GAT  TAA  AAT  ACA  GCA  TGT  AAA  CAT AAA
     ala  ala  asp  ***  asn  thr  ala  cys  lys  his lys
                                                   671
                                                   1951/
                                                   TAT
                                                   tyr
                                                   2011
                                                   GAA

GAT  CGA  TTG  AAT  AGA  TTT  ATG  TTC  AGG  TAC ACA CAT

2071/
                                                        GTA
     AAG  CTT  TTC  TAA  TAA  TAA                   TTC GAA
```

EPITOPIC REGIONS OF PNEUMOCOCCAL SURFACE PROTEIN A

REFERENCE TO RELATED APPLICATION

This application is a continuation-in-part of U.S. patent application Ser. No. 08/246,636 filed May 20, 1994, which itself is a continuation-in-part of U.S. patent application Ser. No. 08/048,896 filed Apr. 20, 1993 now abandoned, which itself is a continuation-in-part of U.S. patent application Ser. No. 07/835,698 filed Feb. 12, 1992, now abandoned, which itself is a continuation-in-part of Ser. No. 07/656,773 filed Feb. 15, 1991, now abandoned.

FIELD OF INVENTION

This invention relates to recognition of epitopic regions of pneumococcal surface protein A (PspA), the major virulence factor of *Streptococcus pneumoniae*.

BACKGROUND OF THE INVENTION

*Streptococcus pneumoniae* is an important cause of otitis media, meningitis, bacterernia and pneumonia. Despite the use of antibiotics and vaccines, the prevalence of pneumococcal infections has declined little over the last twenty-five years.

It is generally accepted that immunity to *Streptococcus pneumoniae* can be mediated by specific antibodies against the polysaccharide capsule of the pneumococcus. However, neonates and young children fail to make an immune response against polysaccharide antigens and can have repeated infections involving the same capsular serotype.

One approach to immunizing infants against a number of encapsulated bacteria is to conjugate the capsular polysaccharide antigens to proteins to make them immunogenic, This approach has been successful, for example, with *Haemophilus influenzae b* (see U.S. Pat. No. 4,496,538 to Gordon and U.S. Pat. No. 4,673,574 to Anderson). However, there are over eighty known capsular serotypes of *S. pneumoniae* of which twenty-three account for most of the disease. For a pneumococcal polysaccharide-protein conjugate to be successful, the capsular types responsible for most pneumococcal infections would have to be made adequately immunogenic. This approach may be difficult, because the twenty-three polyesaccharides included in the presently-available vaccine are not all adequately immunogenic, even in adults, Furthermore, such a vacine would probably be much more expensive to produce than any of the other childhood vaccines in routine use.

An alternative approach for protecting children, and also the elderly, from pneumococcal infection would be to identify protein antigens that could elicit protective immune responses. Such proteins may serve as a vaccine by themselves, may be used in conjunction with successful polysaccharide-protein conjugates, or as carriers for polysaccharides.

In McDaniel et al (I), J.Exp.Med. 160:386–397, 1984, there is described the production of hybridoma antibodies that recognize cell surface proteins on *S. pneumoniae* and protection of mice from infection with certain strains of encapsulated pneumococci by such antibodies. This surface protein antigen has been termed "pneumococcal surface protein A" or PspA for short.

In McDaniel et al (II), Microbial Pathogenesis 1:519–531, 1986, there are described studies on the characterization of the PspA. From the results of McDaniel (II), McDaniel (III), J.Exp.Med. 165:381–394, 1987, Waltman et al., Microb. Pathog. 8:61–69, 1990 and Crain et al., Infect. Immun. 58:3293–3299, 1990, it was also apparent that the PspAs of different strains frequently exhibit considerable diversity in terms of their epitopes, and apparent molecular weight.

In McDaniel et al (III), there is disclosed that immunization of X-linked immunodeficient (XID) mice with non-encapsulated pneumococci expressing PspA, but not isogenic pneumococci lacking PspA, protects mice from subsequent fatal infection with pneumococci.

In McDaniel et al (IV), infect. Immun., 59:222–228, 1991, there is described immunization of mice with a recombinant full length fragment of PspA that is able to elicit protection against pneumococcal strains of capsular types 6A and 3.

In Crain et al, (supra) there is described a rabbit antiserum that detects PspA in 100% (n=95) of clinical and laboratory isolates of strains of *S. pneumoniae*. When reacted with seven monoclonal antibodies to PspA, fifty-Seven *S. pneumoniae* isolates exhibited thirty-one different patterns of reactivity. Accordingly, although a large number of serologically-different PspAs exist, there are extensive cross-reactions between PspAs.

The PspA protein type in independent of capsular type. It would seem that genetic mutation or exchange in the environment has allowed for the development of a large pool of strains which are highly diverse with respect to capsule, PspA, and possibly other molecules with variable structures. Variability of PspA's from different strains also is evident in their molecular weights, which range from 67 to 99 kD. The observed differences are stably inherited and are not the result of protein degradation.

Immunization with an induced isolate of *E. coli* infected with a recombinant λ gt11 clone producing PspA, elicited protection against challenge with several *S. pneumoniae* strains representing different capsular and PspA types, as described in. The protection was assumed to be the result of immunization with the recombinant PspA, since a λ gt II phage lacking the pspA gene failed to elicit protection. McDaniel et al (IV), Infect. Immun. 59:222–228, 1991. Although clones expressing PspA were constructed according to that paper, the product was in low yield and unstable, and isolation or purification from cell wall, cytoplasmic and medium components following lysis was not effected.

While the protein is variable in structure between different pneumococcal strains, numerous cross-reactions exist between all PsPA's, suggesting that enough common epitopes may be present to allow a single PspA or at most a small number of PspA's to elicit protection against a large number of *S. pneumoniae* strains.

In addition to the published literature specifically referred to above, the inventors, in conjunction with co-workers, have published further details concerning PspA's as follows:

1. Abstracts of 89th Annual Meeting of the American Society for Microbiology, p. 125, item D-257, May 1989;
2. Abstracts of 90th Annual Meeting of the American Society for Microbiology, p. 98, item D-106, May 1990;
3. Abstracts of 3rd International ASM Conference on Streptococcal Genetics, p. 11, item 12, June 1990;
4. Talkington et al, Infect. Immun. 59:1285–1289, 1991;
5. Yother et al (I), J. Bacteriol. 174:601–609, 1992;
6. Yother et al (II), J. Bacteriol. 174:610–618, 1992, and
7. McDaniel et al (V), Microbiol Pathogenesis, 13:261–268, 1992.

In the aforementioned copending United States patent applications Ser. No. 656,773 and 835,698 (corresponding to published International patent application, WO 92/1448), as well as in Yother et al (I) and (II), the disclosures of which are incorporated herein by reference, there are described the preparation of mutants of *S. pneumomiae* that secrete an immunogenic truncated form of the PspA protein, and the isolation and purification of the secreted protein. The truncated form of PspA was found to be immunoprotective and to contain the protective apitopes of PspA. The PspA protein described therein is soluble in physiologic solution and lacks at least the functional cell membrane anchor region.

The aforementioned USSNs' also describe characteristics of the mature Rx1 PspA protein. The mature protein in composed of 588 amino acids and has a molecular weight of 65 kD. The N-terminal 288 amino acids are highly charged and predict an a-helical coiled-coil protein structure. The C-terminal 217 amino acids contain the surface anchor of PspA and does not appear to be α-helical. In the middle of the molecule is a proline rich region that in thought to traverse the cell wall.

In the specification which follows and the drawings accompanying the same, there are utilized certain accepted abbreviations with respect to the amino acids represented thereby. The following Table I identifies those abbreviations:

TABLE I

AMINO ACID ABBREVIATIONS

| A = Ala = Alanine | M = Met = Methionine |
|---|---|
| C = Cys = Cysteine | N = Asn = Asparagine |
| D = Asp = Aspartic Acid | P = Pro = Proline |
| E = Glu = Glutamic Acid | Q = Gln = Glutamine |
| F = Phe = Phenylalanine | R = Arg = Arginine |
| G = Gly = Glycine | S = Ser = Serine |
| H = His = Histidine | T = Thr = Threonine |
| I = Ile = Isoleucine | V = Val = Valine |
| K = Lys = Lysine | W = Try = Tryptophan |
| L = Leu = Leucine | Y = Tyr = Tyrosine |

SUMMARY OF INVENTION

In accordance with the present invention, there has been identified a 68-amino acid region of PspA from the Rx1 strain of *Streptococcus pneumoniae* which not only contains protection-eliciting apitopes, but also in sufficiently cross-reactive with other PspA's from other *S. pneumoniae* strains so as to be a suitable candidate for the region of PspA to be incorporated into a recombinant PspA vaccine.

The 68-amino acid sequence extends from amino acid residues 192 to 260 of the Rx1 PspA protein. While the disclosure herein refers specifically to the specific 68 amino acid sequence of the Rx1 PspA protein, any region of a PspA protein from any other *S. pneumoniae* species which is effectively homologous, an defined herein, to this sequence of the Rx1 PspA protein is included within the scope of the invention, for example, from strains D39 and R36A.

Accordingly, in one aspect, the present invention provides an isolated PspA protein fragment comprising amino acid residues 192 to 260 of the PspA protein of the Rx1 strain of *Streptococcus pneumoniae* and containing at least one protectlon-eliciting epitope, and optionally up to a further 40 residues of the protein in the $NH_2$-terminal direction and/or the COOH-terminal direction, or being effectively homologous to such a fragment.

The protein fragment may be one containing an amino acid sequence corresponding to or effectively homologous to the amino acid residues 192 to 260 of the PspA protein of the Rx1 strain and hence may comprise fragments larger or smaller than ones containing the specific amino acid sequence.

In accordance with another aspect of the present invention, an isolated PspA fragment is provided having an amino acid sequence encoded by pneumococcal DNA amplified by polymerase chain reaction (PCR) by oligonuclsotide primers LSM4 and LSM6, an identified in Table III below. This pair of primers is capable of effecting PCR amplification of pneumococcal DNA from a number of strains of *S. pneumoniae*.

The protein fragment of the invention may be produced recombinantly in the form of a truncated C-termrinal deleted product containing the protein fragment, specifically a truncated C-terminal-deleted product containing the approximately C-terminal third of an α-helical region of the native PspA protein, which may be the Rx1 PspA.

The present invention also includes an isolated protein fragment comprising an amino acid sequence corresponding to that of a protein-eliciting epitope contained in amino acid residues 192 to 260 of the PspA protein of the Rx1 strain of *Streptococcus pneumoniae*.

The amino acid sequence of the protein fragment need not be that found in strain Rx1 but can be based on a corresponding sequence from another strain. Thus, the present invention also includes an isolated protein fragment comprising an amino acid sequence corresponding to that of amino acid residues 192 to 260 of the PspA protein of the Rx1 strain of *Streptococcus pneumoniae*.

In particular, the invention includes an isolated protein fragment comprising the amino acid sequence of or effectively homologous with that of a protection-eliciting epitope corresponding to an epitope contained in amino acid residues 192 to 260 of the pneumococcal surface protein A (PspA) protein of the Rx1 strain of *Strgetococcus pneumoniae*, and including no more than 40 additional amino acid residues in the $NH_2$—and/or the COOH-terminal direction.

The term "effectively homologous" used herein means, in relation to an amino acid sequence effectively homologous to a defined sequence, that the said amino acid sequence may not be identical to said defined sequence but may be at least about 70 percent, more preferably about 80 percent, still more preferably about 90 percent identical, provided that the antigenic epitope or epitopes in said amino acid sequence have properties substantially the same an the corresponding epitopes in said defined sequence.

We have further found that a PspA fragment including C-terminal regions of the PspA also contains protection-eliciting epitopes. Accordingly, in a further aspect, the present invention provides an isolated pneumococcal surface protein A (PspA) fragment comprising a C-terminal portion of the PspA protein from amino acid residue 192 and also a C-terminal portion of the PspA protein from amino acid residue 293, up to and including the amino acid residue 588 of the Rx1 strain of *Straptococcus pneumaniae* and containing at least one protection-eliciting epitope and optionally up to a further 25 residues of the protein in the $NH_2$-terminal direction, or being effectively homologous with such a protein fragment.

Further, an additional aspect of the present invention provides an isolated protein fragment comprising the amino acid sequence of or effectively homologous with that of at least one protection-eliciting epitope corresponding to an epitope contained in a C-terminal portion of the pneumococcal surface protein A (PspA) from amino acid residue 192 and contained in a C-terminal portion of the PspA protein from amino acid residue 293, up to and including amino acid residue 588 of the Rx1 strain of *Streptococcus pneumoniae*, and including no more than 25 additional amino acid residues in the NH$_2$-terminal direction.

Certain new monoclonal anti-PspA antibodies are described herein and, accordingly, in an additional aspect of the invention, there is provided a monoclonal anti-PspA antibody selected from those identified by the designations XiR 1526, XiR 35, XiR 1224, XiR 16, XiR 1325 and XiR 1323.

Certain oligonucleotide primers have been constructed for the amplification of pneumococcal DNA and, according to a further aspect of the invention, here is provided an oligonucleotide primer or probe which is LSM1, LSM2, LSM3, LSM4, LSM5, LSM6, LSM7, LSM8, LSM9, LSM10, LSM11, LSM12, LSM13, LSM14, LSM15, LSM16, LSM17 or LSM18, as identified in Table III below.

Pairs of such primers may be used for PCR amplification of pneuniccocal DNA for the production of pneumococcal DNA or the detection of pneumococcal DNA in a sample, comprising a N-terminal primer selected from LSM1, LSM3, LSM44, LSM5, LSM7, LSM8, LSM10, LSM12 and LSM13 and a C-terminal primer selected from LSM2, LSM6, LSM9, LEMl11 and LSM14. FIG. 3 shows the location of the primers in relation to the region of DNA encoding PspA protein.

Specific pairs of such oligcnucleotide primers may be employed to amplify certain regions of the pneumococcal DNA for cloning into an expression vector and expression of the PspA fragment encoded by the amplified DNA. As described below primer pair LSM3 and LSM2 may be used in the production of plasmid like pBC207, primer pair LSM4 and LSM2 may be used in the production of a plasmid like pBC100, primer pair LSM7 and LSM2 may be used in the production of a plasmid like pBAR501, and primer pair LSM4 and LSM6 may be used in the production of a plasmid like pBAR416.

BRIEF DESCRIPTION OF DRAWINGS

FIGS. 1A–1C contains the DNA sequence for the pspA gene of the Rx1 strain of *S. pneumoniae* (SEQ ID NO: 1) with the deduced amino acid sequence for the PspA protein (SEQ ID NO: 2);

GENERAL DESCRIPTION OF INVENTION

As described in the prior U.S. patent applications referred to above (and in corresponding WO 92/1448) and in Yother et al (I) and (II). the pspa gene of strain Rx1 encodes a 65 kDa molecule composed of 588 amino acids.

Figure 1A:
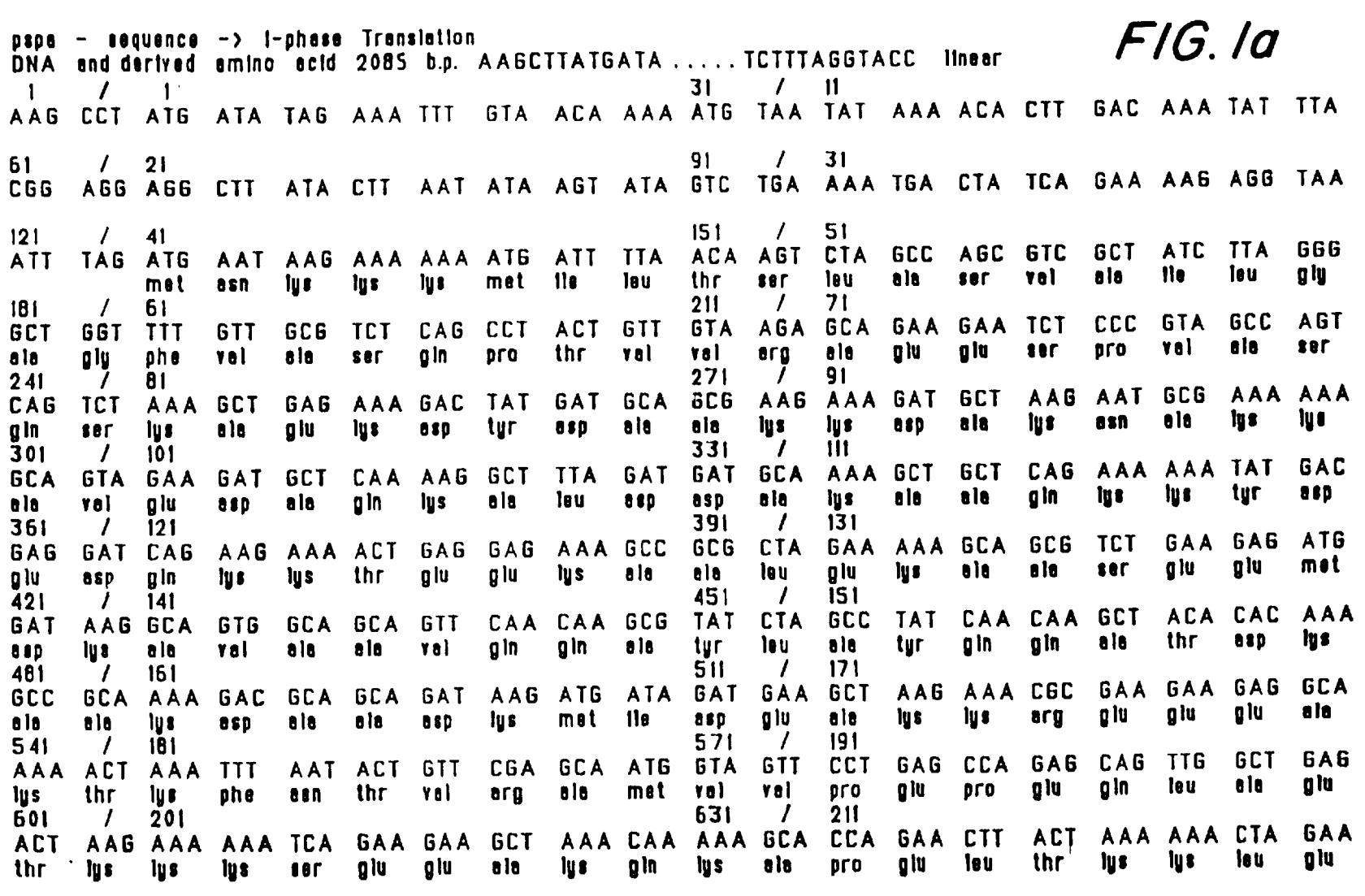

The nucleotide sequence (SEQ ID No: 1) of the pspAgene and derived amino acid sequence (SEQ ID No: 2) are set forth in FIG. 1. The DNA sequence of the pspa gene in contained on a HindIII—KpnI fragment that is 2086 base pairs in length. The pspA gene itself represents 1985 base pairs of the fragment and comprises an initial region containing transcription and translation signals with translation starting at the ATG/met (nucleotide position 127, codon position −31), followed by a leader sequence extending from the ATG/met to GCA/ala (nucleotide position 217, codon −1). Mature Pspa starts with the glu amino acid at nucleotide position 220 (codon +1) and ends at the translational stop TAA/OCH at nucleotide position 1954. This translational stop codon is followed by transcription termination signals.

Figure 2:
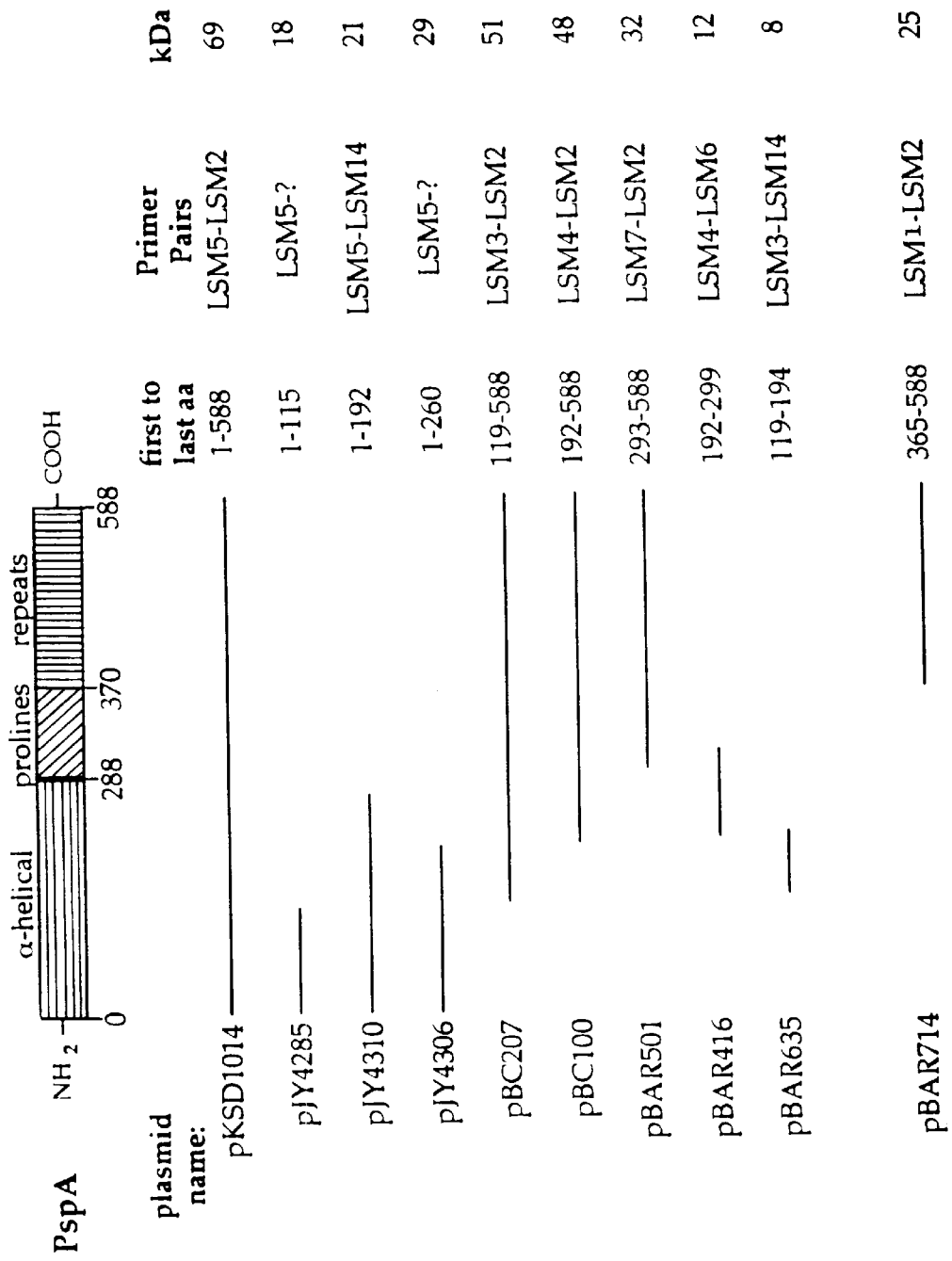
FIG. 2 contains a schematic representation of the domains of mature PspA protein as well as identification of certain plasmids containing gene sequences coding for the full length protein (pKSD 1014), coding for specific segments of the N-terminal portion of the protein (pJY4484 or pJY4285, pJY4310, pJY4306), coding for specific sequences of the C-terminal region of the protein (pBC207, pBC100, pBAR501, pBAR714) and coding for specific intermediate regions of the protein (pBAR416, pBAR635), FIG. 3 contains a schematic representation of the domains of mature PspA protein along with identification of the location of the PCR primer sequences identified herein.
Figure 3:
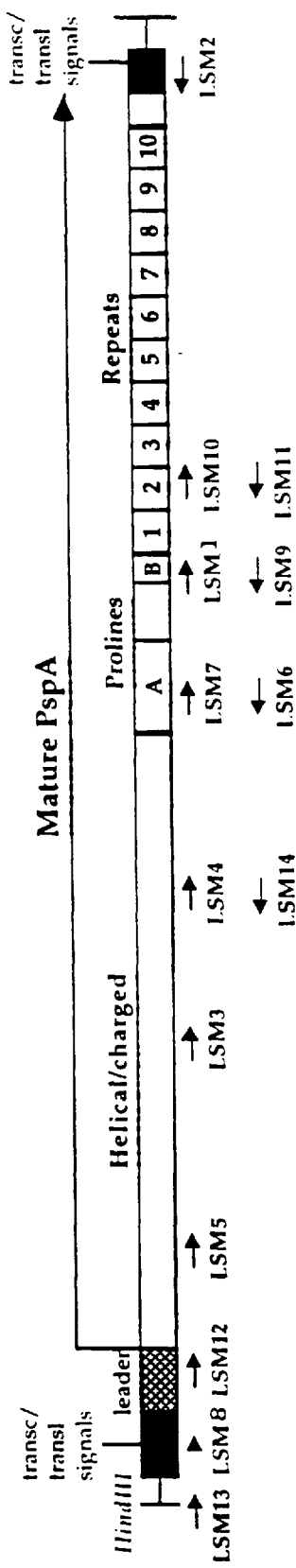

The N-terminal half of the molecule is highly charged and its DNA sequence predicts an α-helical coiled-coil protein structure for this region (288 amino acids), an seen in FIG. 2. The C-terminal half of PspA, which is not α-helical, includes a proline-rich region (83 amino acids) and a repeat region facilitates passage of the molecule through the cell wall or may containing the highly conserved twenty amino acid repeats, as well as a slightly hydrophobic eeouence of 17 amino acids at the C-terminus. It is known that PspA is anchored to *S. pneumoniae* by its C-terminal half and it is likely that the proline-rich region serves to tangle the molecule in the cell wall. In addition, it is anticipated that the highly-charged α-helical region begins at the cell wall and extends into and possibly through the capsule. This model is supported by the observation that the α-helical domain contains all the surface exposed epitopes recognized by monoclonal antibodies (MAbs) reactive with PspA on the pneumococcal surfaces.

The PspA protein of *S. pneumoniae* strain Rx1 has been mapped to locate protection-eliciting epitopes. Such mapping has been effected by employing antibodies to the PspA protein and recombinant fragments of PspA. This mapping technique, described in detail in the Examples below, has identified an amino acid sequence corresponding to the C-terminal third of the α-helical region of PspA as containing protection-eliciting epitopes, specifically the amino acid residues 192 to 260 of the Rx1 PspA protein. The amino acid sequence from residues 192 to 260 is the C-terminal third of the α-helical sequence, expected to be near the cell wall surface.

We have shown that a recombinant PspA fragment from Rx1 consisting of amino acids 192 to 299 (produced by pBAR 416) elicits cross-protection against challenge by a number of different wild-type strains of *S. pneumoniae*. We have also amplified the DNA from sixteen out of sixteen pneumococcal strains using a pair of oligonucleotide primers LSM4 and LSM6 and cloned the amplified DNA of many of these strains.

In addition, recombinant PspA fragments from Rx1 expressed in *E. coli* by pBC100 and consisting of amino acids 192 to 588, i.e. including the C-terminal anchor region, also elicited cross-protection against challenge by a number of wild-type strains of *S. pneumoniae*, showing the presence of protection-eliciting epitopes. Furthermore, recombinant PspA fragments from Rx1 expressed in *E. coli* by pBAR501and consisting of amino acids 293 to 585, i.e. consisting only of the prolines and repeats region elicited cross-protection against challenge by a number of wild-type strains of *S. pneumoniae*, showing the presence of protection-eliciting epitopes in this fragment.

Since the portion of the sequence from residues 192 to 260 contains only 68 amino acids, individual PspA protein fragments of this size may not be optimally antigenic. This difficulty is overcome by producing recombinant proteins containing the 68 amino acids of PspA fused to a non-pneumococcal protein.

Accordingly, in a further aspect of the invention, there is provided a PspA protein fragment comprising a plurality of conjugated molecules, each molecule comprising amino acid residues 192 to 260 of the PspA protein of the Rx1 strain of *Streptococcus pneumoniae* and containing at least one protection-eliciting epitope, each molecule being derived from a different strain of *S. pneumoniae.*

Such tandem molecules may be engineered to maintain proper coiled-coil structure at the points of junction and to be large enough to be immunogenic and to express an array of protection-eliciting epitopes that may cross-react with a wide spectrum of PspAs. Alternatively, individual recombinantly-produced peptides may be attached by chemical means to form a complex molecule.

A further alternative is to attach the PspA fragment to a larger carrier protein or bacterial cell, either an recombinant fusion product or through chemical attachment, such as by covalent or ionic attachment.

The protein fragments, as well an peptide analogs thereof, provided herein are useful components of a vaccine against disease caused by pneumococcal infection. Accordingly, the present invention provides, in a yet further aspect, an immunogenic comnposition comprising at least one PspA protein fragment as defined herein as an immunologically-active component thereof.

We have previously shown that, although PspAs are serologically variable, antisera raised against individual PspAs are sufficiently crows-reactive that they can frequently protect against *S. pneumoniae* which express serologically distinguishable PspAs. We have now shown herein that PspAs from different pneumococcal strains, can protect an animal model from challenge by different pneumococcal isolates. These results indicate that a linited number of serological PspA types may elicit protection against a broad spectrum of different pneumococci.

The immunogenic compositions, including vaccines, provided herein, comprising full-length PappA or the various PspA fragments described herein, elicit an immune response by the host to which it in administered including the production of antibodies by the host.

The immunogenic composition may be prepared as injectables, as liquid solutions or emulsions. The PspA or immunogenic fragment thereof may be mixed with physiologically acceptable carriers which are compatible with the PspA material. These carriers may include water, saline, dextrose, glycerol, ethanol and combinations thereof. The vaccine may further contain auxiliary substances, such as wetting or emulsifying agents, pH buffering agents, or adjuvante to further enhance the effectiveness of the vaccine. Vaccines may be administered by injection subcutaneously or intramuscularly.

Alternatively, the immunogenic compositions comprising full-length PspA or immunogenic fragments thereof formed according to the present invention, may be delivered in a manner to evoke an immune response at mucosal surfaces. Thus, the immunogenic composition may be administered to mucosal surfaces by, for example, the nasal or oral (intragastric) routes. Alternatively, other modes of administration including suppositories may be desirable. For suppositories, binders and carriers may include, for example, polyalkylene glycols and triglycerides. Oral formulations may include normally employed incipients, such an pharmaceutical grades of saccharine, cellulose and magnesium carbonate.

These immunogenic compositions may take the form of solutions, suspensions, tablets, pills, capsules, sustained release formulations or powders and contain 1 to 95% of the microparticles of the present invention.

The immunogenic compositions are administered in a manner compatible with the dosage formulation, and in such amount as to be therapeutically effective, protective and immunogenic. The quantity to be administered depends on the subject to be treated, including, for example, the capacity of the subject's immune system to synthesize antibodies, and if needed, to produce a cell-mediated immune response. Precise amounts of PspA and/or fragment thereof required to be administered depend on the judgement of the practitioner. However, suitable dosage ranges are readily determinable by one skilled in the art and may be of the order of micrograms to milligrams. Suitable regimes for initial administration and booster doses are also variable, but may include an initial administration followed by subsequent administrations. The dosage of the vaccine may also depend on the route of administration and will vary according to the size of the host.

Protein fragments according to the invention may be made in any desired manner. In particular, unique DNA probes may be tailored in known manner for use in a PCR reaction to amplify genomic DNA coding for a desired fragment, the amplified DNA is inserted into a suitable plasmid vector and the vector is utilized in a known manner to express the protein in a suitable host, such as *E. coli*, adopting, for example, the methods taught in Examples 2 and 3 below.

The appropriate PspA fragments may be cloned and expressed and their truncated products expressed under the control of an appropriate promoter, e.g. a vector containing the *E. coli* lac promoter expressing the *E. coli* ompA and leader sequence to create an ompa: :pspA fusion plasmid. Optionally, the sequence coding for the PspA fragment may be linked to a sequence coding for a further protein suitable for injection into humans. Such proteins may be those already used as vaccines, because they are known to elicit protective immune responses and/or known to function as strong immunologic carriers. Such proteins may include the partial or complete amino but are not limited to acid sequence of toxics, such as tetanus toxin, or outer membraine ane proteins, such as that of group B subtype 2 *Neisseria meningitis.*

It is also possible to produce a fusion protein composed of the cross-reactive protection-eliciting regions of several different PspA molecules, as mentioned above. Such a fusion protein may be made large enough (≧40,000 molecular weight) to be highly immunogenic and as a single protein may elicit cross-protection to as many different pneumococci as possible. The combination of croos-protective about 70 amino acid regions from 5 to 6 PspAs would be large enough to be highly immunogenic. Constructs expressing epitopes from more than one PspA are especially attractive since PspAs of pneumococci are known to differ serologically. Present evidence indicates that a widely protective vaccine will need to contain cross-reactive protection-eliciting epitopes from more than one different pneumococcus.

It is possible to design such a fusion protein so that it also carrot a domain that would assist with isolation of the fusion product by including the choline banding region of PspA, or a ligand binding domain from other proteins, such as the maltose binding protein (encoded by malE) of E. coli. In the former case, the fusion protein may be isolated by adsorption to a choline Sepharose® column and elution using 2% choline chloride. In the latter caset adsorption is to an amylose-Sepharose column, followed by elution with a solution containing maltose.

In the construction of such a fusion protein containing tandem cross-reactive coiled-coil PspA regions, it is critical not only that the appropriate open reading frame of each down stream gene fragment be preserved at the junctions of the ligated gene fragments, but that the heptad motif of the coiled-coil amino acid sequence not be disrupted. One way to accomplish the latter is to construct the gene fusions so that they occur within naturally occurring non-coil-coiled regions found in the α-helical domain of PspA. In Yother et al (I), such non-coiled-coil breaks were identified at amino acid positions 169 to 176, 199, 225, 254, 274 and 289. Fusions between two or more cross-protective regions (residues 192–260) at or near positions 170 or 199 at one end and at or near residues 274 or 289 at the other end, can be expected to be able to express the epitopes normally expressed within the coiled-coil regions.

In each case, the simplest way to prepare such constructs is by PCR amplification of the DNA used to construct the gone fusions. In this way, it is possible to prepare the relevant sequence with appropriate restriction sites. The design of gene fusions and the PCR primers used to produce the individual papa fragments will be carried out 60 that the proper reading frame will be preserved in each fused gene fragment at the nucleotido level.

It is also poosible to synthesize peptides according to the invention having the appropriate amino acid sequence by conventional peptide synthesis.

BIOLOGICAL MATERIALS

In the Examples which follow as well an in the accompanying drawinge, reference is made to certain plasmid materials containing whole or truncated pspA gene sequences, The following Table II providem a summary of such materials:

TABLE II

| Plasmid | Identification | Gene Product |
|---|---|---|
| pKSD1014 | whole gene | amino acids 1 to 588 |
| pJY4284 or pJY4285 | 5' terminal region | amino acids 1 to 115 |
| pJY4310 | 5'-terminal region | amino acids 1 to 192 |
| pJY4306 | 5'-terminal region | amino acids 1 to 260 |
| pBC207 | 3'-terminal region | amino acids 119 to 588 |
| pBC100 | 3'-terminal region | amino acids 192 to 588 |
| pBAR416 | internal region | amino acids 192 to 299 |
| pBAR501 | 3'-terminal region | amino acids 293 to 588 |

In addition, reference is made in the following Examples to certain PCR oligonucleotide primer sequence.

Further, the present invention provides certain oligonucleotide primers useful, in combinations, for amplifying selected portions of pneumococcal DNA. In the following Table III is provided identification of the primer, description thereof, the 5' to 3' sequence of the primer and the nucleotide position of the primer sequence on the DNA of the Rx1 strain of *S. pneumoniae*. FIG. 3 also shows the locations of primers LSM1 to LSM14 in relation to the domains of mature PspA protein.

TABLE III

PCR Oligonucleotide Primers

| Designation | Description | Sequence 5' -3' | SEQ ID NO. | Nucleotide Position |
|---|---|---|---|---|
| LSM1 | in the 3' end of the prolines flanking the repeat region | CCg gAT CCA gCT CCT gCA CCA AAA AC | 3 | 1312 to 1331 |
| LSM2 | "The" 3' primer; covers the last 5 amino acids | gCg CgT CgA Cgg CTT AAA CCC ATT CAC CAT Tgg | 4 | 1990 to 1967 |
| LSM3 | within the α-helix | CCg gAT CCT gAg CCA gAg CAg TTg gcT g | 5 | 576 to 598 |
| LSM4 | within the α-helix | CCg gAT CCg CTC AAA gAg ATT gAT gAg TCT g | 6 | 792 to 814 |
| LSM5 | starts internal to "glu" the mature coding sequence | gCg gAT CCC gTA gCC AgT CAg TCT AAA gCT g | 7 | 228 to 253 |
| LSM6 | at the 5' end of the prolines | CTg AgT CgA CTg gAg TTT CTg gAg CTg gAg C | 8 | 1117 to 1093 |
| LSM7 | opposite orientation of LSM6 | CCg gAT CCA gcT CCA gCT CCA gAA ACT CCA g | 9 | 1093 to 1117 |
| LSM8 | covers the −35 sequence | gCg gAT CCT TgA CCA ATA TTT ACg gAg gAg gC | 10 | −79 to −56 (47 to 70) |
| LSM9 | opposite orientation of LSM8 | gTT TTT ggT gCA ggA gCT gg | 11 | 1331 to 1312 |
| LSM10 | within the repeat region | gCT ATg gCT ACA ggT Tg | 12 | 1441 to 1457 |
| LSM11 | opposite orientation of LSM10 | CCA CCT gTA gCC ATA gC | 13 | 1457 to 1441 |
| LSM12 | in the leader peptide sequence | CCg gAT CCA gCg TCg CTA TCT TAg ggg CTg gTT | 14 | 161 to 187 |
| LSM13 | at the HindIII site upstream from the coding region region | gCA AgC TTA TgA TAT AgA AAT TTg TAA C | 15 | 1 to 26 |
| LSM14 | opposite orientation of LSM4 | gCg CgT CTC TTT gAg CTC TTg TTC TAg TCT | 16 | 802 to 778 |
| LSM15 (S) | LSK14 with a stop codon | CGC GTC GAC TCA GAG CTC TTG TTC TAG | 17 | 793 to 781 |
| LSKl6 (S) | 5' to LSM6 with a stop codon | CGC GTC GAC TCA CTC ATT AAC TGC TTT | 18 | 1091 to 1069 |

TABLE III-continued PCR Oligonucleotide Primers

| Designation | Description | Sequence 5'-3' | SEQ ID NO. | Nucleotide Position |
|---|---|---|---|---|
| LSM17 | LSM5 with a different reading frame | gC ggA TCC CgT AgC CAg TCA gTC TAA AgC Tg | 19 | 228 to 253 |
| LSM18 | LSM2 without a stop condon | TAT TTC AgT TAC ggT TAC CAC TTA CCC TTA Agg Cg | 20 | 1990 to 1955 |

EXAMPLES

Example 1

This Example describes the bacterial strains, plasmids and monoclonal antibodies used herein, as well as the procedure for passive immunization of mice using the monoclonal antibodies.

S. pneumoniae strains, identified in Table III below, were grown in Todd Hewitt broth with 0.5% yeast extract at 37° C. or on blood agar plates containing 3% sheep blood in a candle jar. E. coli strain DH1 (Hanahan, J. Mol. Biol. 166:557) was grown in LB medium or minimal E medium. Plasmids included pUC18 (Gene 33:103), pJY4163 (Yother et al (II)), and pIN-III-ompA EMBO J. 3:2437).

All antibody-secreting hybridoma lines were obtained by fusions with non-antibody-secreting myeloma cell line P3-X63-Ag.8.653 (J. Immunol. 123:1548). The specific antibodies employed are identified in Table IV below. The anti-PspA hybridoma cell lines Xi64, Xi126 and XiR278 have previously been described in McDaniel at al (I) and Crain et al (supra). The remaining cell lines were prepared by immunizing CBA/N mice with recombinant D39 PspA expressed in λgtII by the technique described in McDaniel et al (I). The cell lines producing antibodies to PspA were all identified using an ELISA in which microtitration plates were coated with heat-killed (60° C., 30 mins) S. pneumoniae R36A or Rx1, which would select for those MAbs that react with surface exposed epitopes on PspA. The heavy chain isotypes of the MAbs were determined by developing the ELISA with affinity purified goat antibody specific for $\mu$ and $\gamma$ heavy chains of IgM and IgG mouse immunoglobulin. The specificity of the MAbs for PspA was confirmed by immunoblot analysis, All six newly-produced MAbs, identified in Table IV as XiR 1526, XiR 35, XiR 1224, XiR 16, XiR 1325 and XiR 1323, detected a protein of the expected size (apparent molecular weight of 84 kDa) in an immunoblot of strains Rx1 and D39. No reactivity was observed for any of the MAbs in an immunoblot of strain WG44.1, a PspA⁻ variant of Rx1 (see McDanAel et al (III) and Yother et al (II)).

Theee six antibodies along with the previously described antibodies Xi64, Xi126 and XiR278, made up a panel of antibodies used to map epitopes on PspA, as described in Example 5 below.

Five of these antibodies were observed to be able to protect mice from otherwise fatal infection with strain WU2 (see Tables VI and V below).

TABLE IV

Reactivities of MAbs with PspAs from Streptotococcus pneumoniae

| Streptococcus pneumoniae | | | | Monoclonal Antibody (isotype) | | | | | | | | |
|---|---|---|---|---|---|---|---|---|---|---|---|---|
| | | | | XiR1526 | XiR35 | XiR1224 | Xi126 | XiR16 | Xi64 | XiR1325 | XiR278 | XiR1323 |
| Strain | Capsule type | PspA type | Ref. # | (IgG2b) | (IgG2a) | (IgM) | (IgG2b) | (IgG2a) | (IgM) | (IgG2a) | (IgG1) | (IgM) |
| Rx1 | rough | 25 | 36 | ++ | ++ | ++ | ++ | ++ | ++ | ++ | ++ | ++ |
| ATCC101813 | 3 | 3 | 37 | − | − | − | ++ | − | ++ | ++ | ++ | ++ |
| EF19197 | 3 | 18 | 38 | − | − | − | − | − | − | −/+ | ++ | − |
| BG9739 | 4 | 26 | 38 | − | − | − | − | − | − | ++ | + | ++ |
| L81985 | 4 | 23 | 39 | − | − | − | − | − | − | − | − | − |
| BG-5-3A | 6A | 8 | 38 | − | − | + | −/+ | − | − | − | + | + |
| BG9163 | 6B | 21 | 38 | − | − | − | − | − | − | − | + | − |
| MH188 | 22 | ND | * | − | − | − | −/+ | − | − | − | − | − |
| WU2 | 3 | 1 | 39 | − | − | − | ++ | − | ++ | ++ | ++ | ++ |
| Protection against WU2 | | | | − | − | − | + | − | + | + | + | + |

The protective capacity of the MAbs was tested by injecting CBA/N mice i.p. with 0.1 ml of ¹/₁₀ dilution about 5 to 30 $\mu$g) of each MAb 1 hr prior to i.v. injection of $10^3$ CFU of WU2 or D39 pneumococci (>100×LD$_{50}$). MAbs were judged to be protective if they prevented the death of all mice infected with WU2. All mice that did not recieve an infection died of pneumococcal infection within 48 hours post challenge.

Example 2

This Example describes the cloning of fragments of the pspA gene from pneumococcal strain Rx1 by polymerase chain reaction (PCR) and the procedure for immunization of mice by the PspA fragments produced by the cloned fragments.

The design of the PCR primers was based on the sequence of the pspA gene from pneumococcal strain Rx1 (see FIG. 1). Oligonucleotides used as 5'-primers were LSM3, LSM4 and LSM7. LSM3 was 28 bases in length and started at base 576, LSM4 was 31 bases in length and started at base 792, and LSM7 was 31 bases in length and started at bass 1093. All three primers contained an additional BamHI site at their 5' ends. The oligonucleotides used as 3' pspA primers were LSM2 which was 33 bases in length and started at base 1990 and LSM6 which was 31 bases in length and started at base 1117. Both primers LSM2 and LSM6 contained an additional SalI sites at their own 5' ends. The nucleotide sequences for the primers are set forth in Table III above.

Primer pairs LSM3–LSM2 were used to generate pBC207, primer pairs LSM4–LSM2 were used to generate pBC100, primer pairs LSM7–LSM2 were used to generate pBAR501 and primer pairs LSM4–LSM6 were used to generate pBAR416, by the procedure generally outlined below.

Approximately 10 ng of genomic Rx1 pneumococcal DNA was amplified using a 5' and 3' primer pair. The sample was brought to a total volume of 50 μl containing a final concentration of 50 mM KCl, 10 mM tris-HCl (pH 8.3), 1.5 mM $MgCl_2$, 0.001% gelatin, 0.5 mM each primer and 200 mM of each deoxynucleouide triphomphate and 2.5 U of Tag DNA polymerame. Following overlaying of the samples with 50 μl of mineral oil, the samples were denatured at 94° C. for 2 mins and then subjected to 10 cycles consisting of 1 min. at 94° C., 2 min. at 50° C. and 3 min. at 72° C., followed by another 20 cycles of 1 min. at 94° C., 2 min. at 60° C. and 3 min. at 72° C. After completion of the 30 cycles, the samples were held at 72° C. for an additional 5 min., prior to cooling to 4° C.

Using primers LSM4 and LSM6 following the procedure described above, it has been possible to amplify the corresponding regicn from sixteen out of sixteen different *S. pneumoniae* strains, namely D39, WU2, BG9739, L81905, DBL6A, DBL5, BG9163, A66, EF6796, BG7322, EF5668, BG7376, LM100, BG6796, BG5-8A and R36A. In addition, the amplified fragments of some of these strains have been cloned, namely D39, WU2, BG9739, DBL6A, DBL5, A66, EF5668, LM100 and R36A.

Example 3

This Example describes expression of N-terminal PspA molecules.

3'-deleted PspA that express N-terminal fragments in *E. coli* and which secrete the same fragments from pneumococci were constructed as described in the aforementioned U.S. patent applications Ser. Nos. 835,698 and 656,773 (sea also Yother et al (II), supra).

For expression of the internal fragment, BAR416, and the 5'-deleted pspA constructs, the secretion vector pIN-III-ompA was used. Amplified pspA fragments were digested with BamHI and SalI and ligated into the appropriately BamI/SalI- digested pIN-III-ompA vector, providing the inserted fragment fused to the ompA leader sequence in frame and under control of the lac promoter. Transformants of *E. coli* DH1 were selected on minimal E medium supplemented with casamino acids (0,1%), glucose (0.2%) and thiamine (0.05 mM) with 50 μg/ml of ampicillin.

Figure 4:
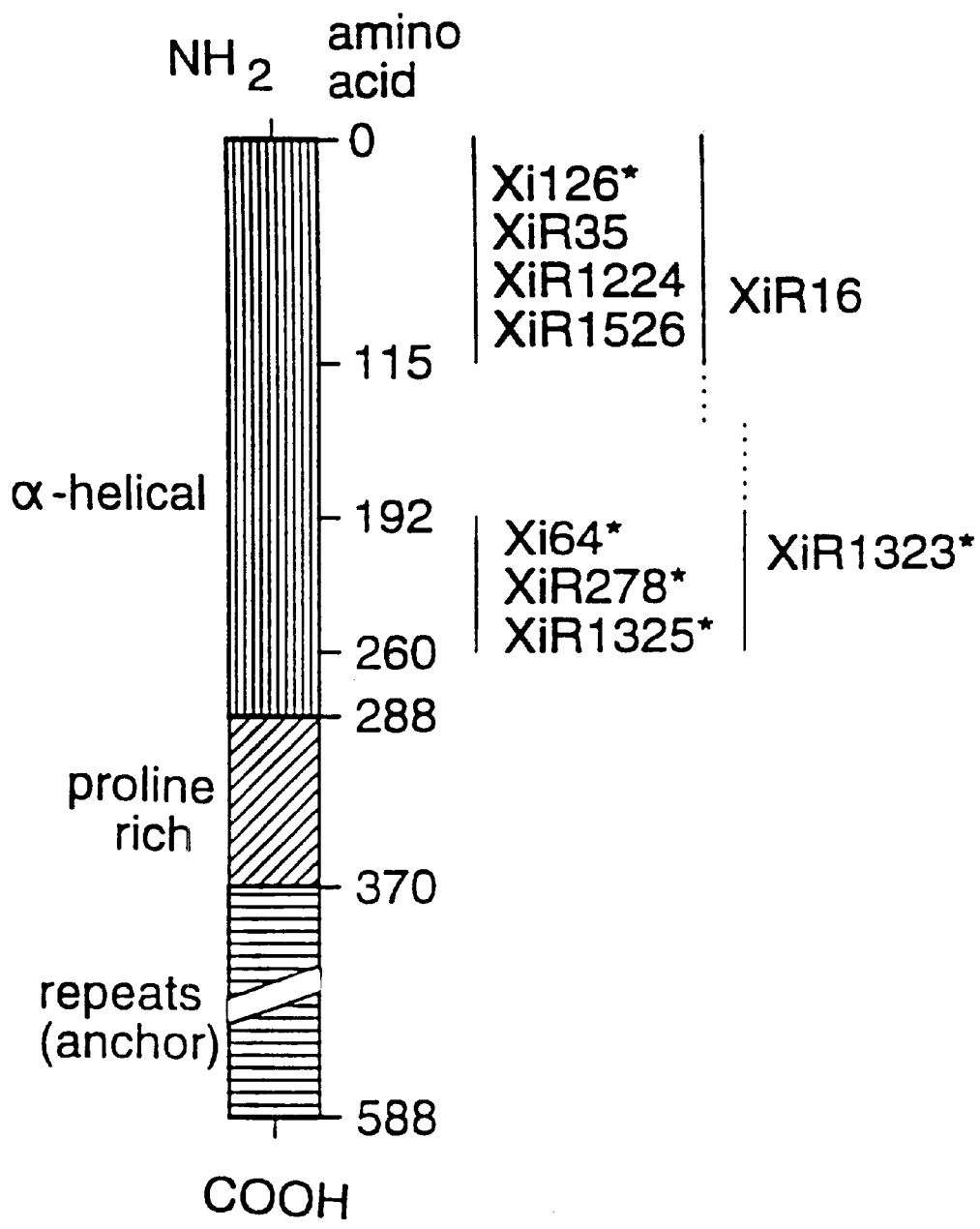
FIG. 4 contains a schematic representation of the domains of the mature PspA protein and the general location of epitopes recognized by certain monoclonal antibodies.

For induction of lac expression, bacteria were grown to an optical density of approximately 0.6 at 660 nm at 37° C. in minimal E medium and ITPG was added to a concentration of 2 mM. The cells were incubated for an additional two hours at 37° C., harvested and the periplasmic contents released by osmotic shock. An immunoblot of the truncated PspA proteins produced by the various plasmids is shown in FIG. 4.

By these procedures, there were provided, for the 3'-deleted pspA, plasmids pJY4284, pJY4285, pJY4310 and pJY4306, the internal fragment, pBAR416 and for the 5'deleted pspAs, plasmids pBC207, pBC100 and pBAR501. Plasmid pJY4284 and pJY4285 contain an insert of 564 base pairs, nucleotides 1 to 564 and encoded a predicted 18 kDa PspA C-terminal-deleted product corresponding to amino acids 1 to 115. Plasmid pJY4310 contains an insert of 795 base pairs, nucleotides 1 to 795 and encoded a predicted 21 kDa C-terminal-deleted product corresponding to amino acid 1 to 192. Plasmid pJY4306 contained an insert of 999 base pairs, nucleotides 1 to 999 and encoded a predicted 29 kDa C-terminal-deleted product corresponding to amino acids 1 to 260. Plasmid pBC100 contained an insert of 1199 base pairs, nuclootides 792 to 1990, and encoded a predicted 48 kDa PspA N-terminal deleted product containing amino acids 192 to 588. pBC207 contained an insert of 1415 base pairs, nucleotides 576 to 1990, and encoded a predicted 51 kDa PspA N-terminal deleted product containing amino acids 119 to 588. pBAR501 contained an insert of 903 base pairs, nucleotides 1093 to 1990, and encoded a predicted 32 kDa PspA N-terminal deleted product containing amino acids 293 to 588. Plasmid pBAR416 contained an insert of 326 base pairs, nucleotides 792 to 1117, and encoded a predicted 12 kDa PspA internal molecule containing amino acids 192 to 299.

The pspA gene sequences contained in these plasmids code for and express amino acids as identified in FIG. 2.

Immunization of CBA/N mice with PspA fragments produced from the plasmids described in this Example was effected by subcutaneous injection in the subinguinal area with an osmotic preparation of the PspA fragment emulsified 1:1 in Complete Freund's Adjuvant (CFA). After 14 days, the mice were injected intraperitoneally with antigen diluted 1:1 in Ringer's lactate without CFA. Seven days later, the mice were challenged intravenously with at least 100 times the $LD_{50}$ of pneumococcal strain WU2. The survival of mice was monitored for 10 days.

Example 4

This Example describes the procedure of conducting immnnunoassays.

Immunoblot analysis was carried out as described in McDaniel et al (IV). The truncated PspA molecules prepared an described in Example 3 or pneumococcal preparations enriched for PspA (as described in McDaniel et al (II)) were electrophoresed in a 10% sodium dodecyl sulfate polyacrylamide gel (SDS-PAGE) and electroblotted onto nitrocellulose. The blots were probed with individual MAbs, prepared as described in Example 1.

A direct binding ELISA procedure was used to quantitatively confirm reactivities observed by immunoblotting. In this procedure, osmotic shock preparations were diluted to a total protein concentration of 3 μg/ml in phosphate buffered saline (PBS) and 100 μl was added to wells of Immulon 4 microtitration plates. After blocking with 1% bovine serum albumin in PBS, unfractionated tissue culture supernates of individual MAbs were titered in duplicate by 3-fold serial dilution through 7 wells and developed as described in McDaniel et al (IV) using a goat anti-mouse immunoglobulin alkaline phosphate conjugated secondary antibody and alkaline phosphate substrate. Plates were read in a DYNATECH (Trademark) plate reader at 405 nm, and the 30% end point was calculated for each antibody with each preparation.

Example 5

This Example describes mapping of the epitopes on PspA using the monoclonal antibodies prepared as described in Example 1.

The six newly-produced monoclonal antibodies described in Example 1 and identified in Table IV were used along with the previously-described monoclonal antibodies Xi64, Xi126 and XiR278 to map epitopes on PspA.

The reactivity of the MAb was determined by two methods. In one method, reactivity between the fragments and MAb was evaluated in immunoblots of the fragment preparations after they had been separated by SDS-PAGE. In the second method, a direct ELISA was used to quantify the reactivity of the MAbs with non-denatured PspA fragment.

To determine whether each of the MAbs recognized different epitopes, each of them was reacted with eight additional *S. punemoniae* strains, as identified in Table IV, in immunoblots of SDB-PAGE separated proteins. Seven different patterns of activity were observed. Three antibodies, XiR16, XiR35 and XiR1526, appeared to recognize epitopes found on Rx1 PspA but none of the other PspAs. Accordingly, it was possible that these three antibodies might all react with the same epitope as Rx1 PspA.

the D39 strain, at the concentrations tested. Nonetheless immunization of mice with Rx1 PspA elicits protection against A66, WU2 and EF6796 strains (mouse virulent pneumococci of capsular types 3, 3 and 6A respectively), all of which have PspA types that are different from those of Rx1 and D39 (see McDaniel et al (IV)). In view of the close serologic similarity between the type 25 PspA of Rx1 and type 1 PspA of WU2 (Crain et al), WU2 pneumococci were used to challenge mice that had been passively protected with the MAbs. All five of the MAbs that were observed to bind WU2 PspA were able to protect against infection with 1000 CFU of WU2. Protective antibodies were found in IgM, IgG1, IgG2b and Ig2a heavy chain isotype classes.

The results are given in the following Table V:

TABLE V

Immunoblot reactivities of monoclonal antibodies with PspA from *Streptococcus pneumoniae* strains Rx1[a] and WU2[b]

| Streptococcus pneumoniae | | Monoclonal antibody (isotype) | | | | | | | |
|---|---|---|---|---|---|---|---|---|---|
| Strain | PspA type | XiR1526 ($IgG_{2b}$) | XiR35 ($IgG_{2a}$) | XiR1224 (IgM) | Xi126 ($IgG_{2b}$) | XiR16 ($IgG_{2a}$) | Xi64 (IgM) | XiR1325 ($IgG_{2a}$) | XiR278 ($IgG_1$) | XiR1323 (IgM) |
| Rx1[a] | 25 | + | + | + | + | + | + | + | + | + |
| WU2[b] | 1 | − | − | − | + | − | + | + | + | + |
| Protection against WU2 infection[c] | | 0/2 | 0/2 | 0/2 | 10/0 | 0/2 | 10/0 | 8/0 | 10/0 | 2/0 |

[a]Rx1 is an non-encapsulated avirulent laboratory strain.
[b]WU2 is a mouse-virulent capsular type 3 strain.
[c]Mice were given antibody intrapertioneally one hour before intravenous challenge with 100 × $LD_{50}$ of WU2. The results are expressed as number of mice alive/number of mice dead after 14 days. Thirty control mice did not receive antibody and only one survived challenge with WU2.

MAb xi64 and Xi126 both reacted strongly only with epitopem on ATCC 101813, WU2 and Rx1 PspAs, but not with PspAs of the other strains. However, it is known from studies of larger panels of PspAs (as described in McDaniel et al (III) and Crain et al) that Xi126 and Xi64 recognize different determinants.

The remaining four antibodies each exhibited unique patterns of reactivity with the panel of PspAs. Accordingly, the nine antibodies tested recognized at least seven different epitopes on PspA.

For reasons which are not clear, the type 2 strain D39 appeared to be uniquely able to resist the protective effects of antibodies to PspA (McDaniel et al (IV)). As described in McDaniel et al (I), greater than forty times the amount of Xi126 was required to passively protect against the D39 strain as compared to the WU2 strain. None of the six newly-produced monoclonal antibodies protected against Example 6

This Example describes mapping of the epitopes of PspA using the recombinant truncated PspA molecules formed in Example 3.

The five-overlapping C-terminal or N-terminal deleted PspA fragments, prepared as described in Example 3 and shown in FIG. 2, were used to map epitopes on PspA. The general location of the epitopes detected by each of the mice MAbs, as described in Example 5, was determined using five C-terminal-deleted and two N-terminal deleted PspA molecules. As a positive control, the reactivity of each antibody was examined with a clone, pKSD1014, expressing full-length PspA. As a negative control, a lysate of *E. coli* containing the vector pIN-III-ompA was used.

The reactivities observed and the quantification of such activity is set forth in the following Table VI:

TABLE VI

Table VI: Reactivity of PspA Fragments with Monoclonal Antibodies[1]

| PspA Fragments[2] | Monoclonal Antibodies | | | | | | | | |
|---|---|---|---|---|---|---|---|---|---|
| | Xi126 | XiR35 | XiR1526 | XiR1224 | XiR16 | XiR1323 | Xi64 | XiR1325 | XiR278 |
| pJY4285 (1–115) | ++ 72 | ++ 5 | ++ <3 | + <3 | + 4 | − <3 | − <3 | − <3 | − <3 |
| pJY4310 (1–192) | ++ 116 | ++ 4 | ++ <3 | + 5 | ++ 16 | − 31 | − <3 | − <3 | − <3 |

TABLE VI-continued

Table VI: Reactivity of PspA Fragments with Monoclonal Antibodies[1]

| PspA Fragments[2] | Monoclonal Antibodies | | | | | | | | | | | | | | | | | |
|---|---|---|---|---|---|---|---|---|---|---|---|---|---|---|---|---|---|---|
| | Xi126 | | XiR35 | | XiR1526 | | XiR1224 | | XiR16 | | XiR1323 | | Xi64 | | XiR1325 | | XiR278 | |
| pJY4306 (1–260) | ++ | 1127 | ++ | 78 | ++ | 554 | ++ | 805 | ++ | 2614 | ++ | <3 | ++ | 643 | ++ | 717 | + | <3 |
| pBC207 (119–588) | – | <3 | – | <3 | – | <3 | – | <3 | + | <3 | ++ | 61 | ++ | <3 | ++ | <3 | ++ | 4527 |
| pBC100 (192–588) | – | <3 | – | <3 | – | <3 | – | <3 | – | <3 | ++ | 15 | ++ | 709 | ++ | 4401 | ++ | 4746 |
| Rx1 (1–588) | ++ | 63 | ++ | 15 | ++ | 42 | ++ | 48 | ++ | 118 | ++ | 44 | ++ | 64 | ++ | 111 | ++ | 466 |
| pIN-III (none) | – | <3 | – | <3 | – | <3 | – | <3 | – | <3 | – | <3 | – | <3 | – | <3 | – | <3 |

1. Antibodies were reacted with the indicated PspA fragments in immunoblot of SDS-PAGE separations, or by ELISA using microtitration plates coated with preparations enriched for the indicated PspA fragments. Rx1 PspA serves as a positive control, and pIN-III-ompA (vector alone) serves as a negative control. The results of the immunoblot are presented as ++ (strong reaction). + (weak but clearly positive reaction) and – (no reaction). ELISA values are given as the reciprocal dilution of each monoclonal antibody that gave 30% of maximum binding with wells coated with the indicate fragment preparation.
2. Plasmids are listed that encode PspA fragments with amino acid residues shown in parenthesis.

The deduced locations of the epitopes are indicated in FIG. 4.

Figure 5:
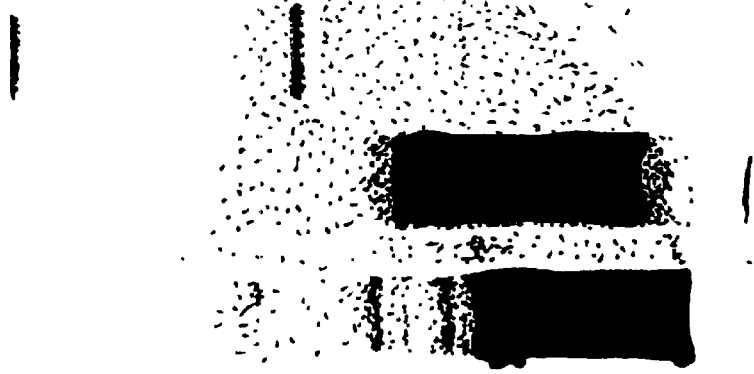
FIG. 5 is an immunoblot of PspA protein gene products produced by plasmids identified therein.

As can be seen from the data in Table VI, three of the antibodies, Xi126 and XiR35 and XiR1526, react strongly with all three C-terminal-deleted clones in immunoblot analysis (FIG. 5), indicating that the sequence required to form the epitope(s) detected by all three lies within the first 115 amino acids of PspA. This map position is in agreement with the failure of these antibodies to react with either of the N-terminal-deleted clones that lack the first 119 and 191 amino acids.

MAb XiR1224 reacted strongly by immunoblot with the longest C-terminal-deleted fragment (pJY4306), but showed substantially weaker reactions with the shorter two C-terminal-deleted fragments. This result indicates that, while the binding site of the antibody may be in the first 115 amino acids, residues beyond amino acid 192 may be important for the conformation or stability of the epitope.

By immnunblot, the three antibodies Xi64, XiR1325 and XiR278, all reacted with the longest C-terminal-deleted fragment and both of the N-terminal-deleted fragments, thus locating their determinants between amino acid positions 192 and 260. Generally confirmatory results were obtained in ELISAs with the native molecules, as described above. However, in a few cases, reactions were observed in ELISAs with full length PspA but not with a truncated molecule even though the same truncated fragment was reactive with the antibody by immunoblot. These observations may have resulted from an altered conformation of the truncated fragments under physiologic conditions that masked or prevented the formation of determinant present in full-length PspA and in the denatured fragments.

Two antibodies, XiR216 and XiR1323, showed what, at first appeared to be anomalous reactions, indicating that epitopes detected by the antibodies might be in more than one portion of PspA. In view of this unexpected result, the assays were repeated multiple times with two sets of preparations of the truncated fragments. The results of the additional assays confirmed the two-position mapping of epitopes for these two MAbs. The data presented in Table VI represents the consensus results of these multiple repeated assays.

By immunoblot, MAb XiR16 reacted strongly with the two longest C-terminal-deleted fragments and failed to react with the shortest N-terminal-deleted fragment. Accordingly, the epitope detected must be N-terminal to position 192. Unexpectedly, MAb XiR16 reacted weakly in immunoblots with both the longest N-terminal-deleted fragment (residues 119 to 158) and the shortest C-terminal-deleted fragment (residues 1 to 115). Since the fragments do not overlap, and if the weak immunoblot reactivities with fragments (reactivities not seen by ELISA) are not an artifact, the MAb XiR16 must recognize epitopes on both fragments.

In the case of MAb XiR1323, the immunoblot data clearly places the detected epitope between positions 192 and 260. In the ELISA studies, however, XiR1323 reacted strongly and reproducibly with the C-terminal-deleted fragment pJY4310 (amino acid residues 1 to 192) as well as the shortest N-terminal-deleted fragment pBC100 (amino acid residues 192 to 588). Curiously, an ELISA reaction was not observed between MAb XiR1323 and pJY4306 (amino acid residues 1 to 260), even though MAb XiR1323 reacted strongly with this fragment by immunoblot.

These findings provide additional evidence for distal conformation effects on antigenic determinants of PspA. They also indicate that, on the native fragments, MAb XiR1323 sees epitopes on both sides of position 192. The relationship between expression of the epitopes in other PspAs and their position in Rx1 PspA is demonstrated in Table VI in which is listed the antibodies in accordance with their apparent map position in PspA. The five antibodies (including XiR16) that clearly recognize epitopes N-terminal to position 116 are listed at the left side of Table VI. The four antibodies that clearly recognize epitopes C-terminal to position 192 are listed on the right side of Table VI. Three of the five epitopes N-terminal of position 192 (those recognized by XiR1526, XiR35, and XiR16) were not found on any of the other eight PspAs tested. One epitope (recognized by XiR 1224) was weakly expressed by one other strain and another (recognized by Xi126) was expressed on two other strains. In contrast, the four epitopes present in the C-terminal third of the PspA α-helical region were each present in from two to six other strains. The greater conservation of the region C-terminal to position 192, as compared to the region N-terminal to position 192 was significant at $P<0.05$ by both the Chi-square and the two sample rank tests. Based on the mapping results (Table IV) and the strain distribution results (Table VI), it is apparent that all of the antibodies except possibly XiR35 and XiR1526 must recognize different PspA determinants.

Example 7

This Example contains a discussion of the mapping results achieved in Example 6.

The results set forth in Example 6 clearly demonstrate that the protection eliciting epitopes of PspA are not restricted to the N-terminal end of the surface exposed α-helical half of the molecule. In fact, four of the five antibodies protective against *S. pneumoniae* WU2 reacted with the C-terminal third of the α-helical region of PspA. This portion of the α-helical region is thought to closest to the cell wall (see Yother et al (II)).

Five of the nine MAbs recognized determinants N-terminal to amino acid 115 and the other half recognized epitopes C-terminal to residue 192. Since the nine antibodies were selected for their ability to bind native PspA on the surface of heat-killed whole pneumococci, the distribution of the epitopes they recognize suggests that determinants between positions 115 and 192 may either not immunogenic or are not exposed on the native molecule as expressed on pneumococci.

Two MAbs (XiR16 and XiR1323) appeared to possibly react with epitopes in more than one position on PspA. Although the bulk of the data for XiR16 placed its epitope N-terminal of position 115, weak immunoblot patterns suggested that a reactive epitope(s) may also exist C-terminal to residue 115. In the case of XiR1323, the bulk of the data indicated that its epitope is between positions 192 and 260. However, the ELISA assay showed significant reactivity of the antibody with a C-terminal-deleted PspA fragment extending from residues 1 to 192. In the case of XiR1323, the antibody reacted with the epitope on the 1 to 192 fragment under natured but not denatured conditions. This may indicate that the epitope is conformational and may not have the same exact sequence as the epitope recognized (under both natured and denatured conditions) between residues 192 and 260. Although there are no extensive repeats in the N-terminal half of PspA, there are a few short repeated sequences that occur more than once in the coiled-coil motif. One such sequence is glu-glu-ala-lys which starts at amino acid positions 105, 133, and 147 and another is lys-ala-lys-leu starting at positions 150 and 220 (see FIG. 1).

One mechanism that may account for the lack of exposure of epitopes between amino acid 115 and 192 would be a folding back of this portion of the α-helical sequence on itself or other parts of PspA to form a coiled-coil structure more complex than a simple coiled-coil dimer. If this occurred, it could explain how PspA tertiary structure can sometimes be dependent on distant PspA structures. A suggestion that tertiary structure might be affected by distant epitopes might, in fact, be the came comes from the observation that some of the truncated forms did not express certain epitopes under physiologic conditions that were detected on the whole molecule under the same conditions and were shown to be present in the fragment after denaturation in SDS.

The presence of protection-eliciting epitopes C-terminal of residue 192 was confirmed by immunizing mice with the PspA fragments produced by pBC100 (amino acids 192 to 588) and pBAR416 (amino acids 192 to 299) (see Example 8 below). The protection elicited by the 192 to 588 fragment made it clear that there were protection-eliciting epitopes C-terminal of amino acid 192. The protection-elicited by fragment 192 to 299 demonstrated that there were protection-eliciting epitope(s) within this portion of the α-helical region.

Since a PspA vaccine may need to contain fragments of several serologically different PspAs, it would be desirable to include in a vaccine only those portions of each PspA that are most likely to elicit cross-protective antibodies. Based on the results presented herein with Rx1 PspA, it appears likely that the portion of the PspA sequences corresponding to residues 192 to 260 of Rx1 PspA is the best known portion of PspA to include in a recombinant PspA vaccine. The epitopes in this portion of PspA were three and a half times as likely to be present in the PspAs of other strains as the epitopes in the residue 1 to 115 portion of the sequence, and none of the 9 antibodies studied clearly reacted with the middle third of the α-helical region.

Example 8

This Example shows cross-protection of an animal model against challenge by a variety of virulent pneumococcal strains by recombinant PspA fragments.

Five mice were immunized with purified PspA fragment produced by pBC207 (produced as described in Example 3) in *E. coli*, and five with PspA purified fragment produced by pBC100 (produced as described in Example 3) in *E. coli*. In both cases, the fragments were injected in Freund's Complete Adjuvant, boosted two weeks later with the fragment in saline and challenged 7 days post boost. All mice immunized with each fragment survived challenge with 100×LD$_{50}$ of WU2 capsular type 3 *S. pneumoniae*.

Five additional control mice were injected with adjuvant plus an equivalent preparation of non-PspA producing *E. coli* (KSD1500-DH1 containing plasmid vector but no insert). All of these control mice died when challenged with the same dose of WU2 strain. These results are consistent with the mapping data since the fragments produced by pBC100 and pBC207 each contained the 192 to 260 region.

As may be seen from this Table VII, protection was afforded against challenge in many instances and in others the life was extended.

In addition, further numbers of mice were immunized with purified fragment produced by pBC100 in *E. coli* following the protocol described above. The mice were challenged with a variety of virulent strains and the pBC100 fragment was found to protect mice against 7 of 14 virulent strains and to extend life for the other 7 strains. The results obtained, which includes the result for the WU2 challenge, are set forth in the following Table VIII:

TABLE VIII

Protection Mediated by Recombinant (BC100) (amino acids 192–588) PspA from strain Rx1

| Challenge strain | Serotype | | Alive:Dead | | Median Day of Death | |
|---|---|---|---|---|---|---|
| | Caps | PspA | BC100 (rPspA) | none | BC100 (rPspA) | none |
| D39 | 2 | 25 | 0:5 | 0:3 | 5 | 2 |
| WU2 | 3 | 1 | 4:0 | 0:3 | >21* | 3 |
| A66 | 3 | 1.3 | 4:0 | 0:3 | >21* | 1 |
| EF10197 | 3 | 18 | 5:0 | 0:3 | >21* | 2 |
| ATCC6303 | 3 | 7 | 5:0 | 0:5 | >21** | 5 |
| EF5668 | 4 | 12 | 1:3 | 0:3 | 9.5 | 4 |
| EF3296 | 4 | 20 | 1:3 | 0:3 | 5 | 3 |
| L81905 | 4 | 23 | 1:5 | 0:6 | 5* | 2.5 |

TABLE VIII-continued

Protection Mediated by Recombinant (BC100)
(amino acids 192–588) PspA from strain Rx1

| Challenge strain | Serotype | | BC100 Alive:Dead (rPspA) | none | Median Day of Death BC100 (rPspA) | none |
|---|---|---|---|---|---|---|
| | Caps | PspA | | | | |
| BC9739 | 4 | 26 | 0:4 | 0:3 | 7 | 2 |
| DBL5 | 5 | 33 | 0:5 | 0:3 | 5* | 2 |
| BG7322 | 6 | 24 | 4:0 | 1:3 | >21* | 6 |
| EF6796 | 6A | 1 | 4:0 | 0:3 | >21* | 1 |
| DBL6A | 6A | 19 | 5:0 | 0:3 | >21* | 7 |

*, different from "none" at $P \leq .004$ in one tailed tests,
**, different from "none" at $P \leq .05$ one tailed tests, all are Fisher exact except DBL5 and L81905 where the one tailed two sample rank test was used.

Further, additional mice were immunized with a purified PspA fragment (pBAR 416) produced by E. coli and corresponding to amino acids 192 to 299, following the protocol described above and challenged with various strains of S. pneumoniae against which protection was provided by the pBC100-derived fragment. The mice immunized with the PspA fragment exhibited an anti-PspA titre of 1/750 by ELISA. Control mice immunized with an osmotic shock preparation from KSD1500 had an anti-PspA titre of <1/10.

The results obtained are contained in the following Table VIII:

TABLE VIII

Protection Mediated by Recombinant pBAR416
(amino acids 192–299) PspA from strain Rx1

| Challenge strain | Serotype | | BAR416 Alive:Dead (rPspA) | none | Median Day of Death BAR416 (rPspA) | none |
|---|---|---|---|---|---|---|
| | Caps | PspA | | | | |
| WU2 | 3 | 1 | 4:1 | 0:4 | >21 | 3 |
| A66 | 3 | 13 | 5:0 | 0:5 | >21 | 2 |
| BG7322 | 6B | 24 | 3:2 | 0:4 | >21 | 7 |
| ATCC6303 | 3 | 7 | 2:3 | 1:4 | 13 | 4 |
| EF6796 | 6A | 1 | 3:2 | 0:5 | >21 | 5 |
| DBL6A | 6A | 19 | 0:5 | 0:5 | 7 | 2 |

The strains tested are all strains protected against by immunization with BC100. The results indicate that the region from 192–260 is able to elicit much of the cross-protection elicited by BC100.
Infected with $\geq 100 \times LD_{50}$ of each strain. In all cases this is $\geq 10^3$ CFU.

The data presented in this Example conclusively proves that epitopes C-terminal to amino acids 119 and 192 respectively are capable of eliciting protective immunity. This result is consistent with the findings presented in the earlier Examples from epitope mapping that the region of PspA from amino acids 192 to 260 contains at least one protection-eliciting epitope.

Example 9

This Example shows cross-protection of an animal model against challenge by a C-terminal fragment of PspA including only proline and repeat regions.

Mice were immunized with the purified PspA fragment produced by pBAR501 (produced as described in Example 3) in E. coli using the protocal set forth in Example 8. Control mice were immunized with an identical preparation that did not contain any PspA. Both groups of mice were challenged with approximately $100 \times LD_{50}$ of various strains of S. pneumoniae.

The results obtained are shown in the following Table IX:

TABLE IX

Cross-protection of mice immunized with BAR501
(proline/repeats region)[a].

| Challenge Strain | Capsular Serotype | PspA Serotype | BAR501 # of mice alive/# dead | BAR501 # of mice alive/# dead | P value |
|---|---|---|---|---|---|
| WU2 | 3 | 1 | 0/10 | 10/0 | <0.0001 |
| A66 | 3 | 13 | 0/5 | 5/0 | <0.008 |
| DBL6A | 6A | 19 | 0/5 | 5/0 | <0.008 |
| EF6796 | 6A | 1 | 1/5 | 1/4 | N.S. |

[a].Mice were immunized with BAR501 or an identical preparation that did not contain any PspA. They were challenged with approximately $100 \times LD_{50}$ of the indicated strains.

The data seen in Table IX shows that the C-terminal PspA fragment produced by pBAR501 confers cross-protection against a variety of virulent pneumococcal strains.

Example 10

This Example shows the cross-protection of an animal model against challenge by a variety of pneumococcal strains by full-length recombinant PspA's.

Five mice were immunized with purified full length recombinant PspA from the EF5668 strain of Streptococcus pneumoniae, expressed in E. coli. The PspA was injected subcutaneously in Freund's complete adjuvant, boosted two weeks later with the whole length PspA in incomplete Freund's adjuvant, and challenged intravenously 7 days post boost, with $100 \times LD_{50}$ of the virulent strain.

The results obtained are shown in the following Table X

TABLE X6

Protection Mediated by Recombinant full-length PspA from Strain EF5668

| Challenge strain | Serologic type | | Alive:Dead | | Median Day of Death | | P value |
|---|---|---|---|---|---|---|---|
| | Capsule | PspA | (rPspA) | no PspA | (rPspA) | no PspA | |
| WU2 | 3 | 1 | 8:0 | 0:7 | >10 | 2 | <0.001 |
| A66 | 3 | 13 | 4:1 | 0:4 | >10 | 2.5 | <0.05 |
| EF5668 | 4 | 12 | 5:0 | 1:4 | >10 | 2 | <0.01 |
| BG7322 | 6 | 24 | 5:1 | 1:5 | >10 | 7 | <0.025 |
| D39 | 2 | 25 | 3:2 | 0:5 | >10 | 3 | N.S. |

Challenge was with 1000 CFU in XID mice (in all cases $\geq 100X$ the $LD_{50}$).

As may be seen from the Tables X immunization with PspA from strain EF5668 also provided crose-protection against a number of strains. Immunization with EF5668 provided against death with EF5668 whereas immunization with RC100 PspA (from strain Rx1) only delayed death with strain 5668. These results indicate that the protection elicited by some PspAs may complement that of others. Since both BC100 and EF5668 PspA protected against a majority of strains, it seems likely that a limited number of serological PspA types may elicit protection against a broad spectrum of different pneumococci. This data also substantiates the potential use of PspA as an important component of a protein-based pneumococcal vaccine.

Summary of the Disclosure

In summary of this disclosure, the present invention provides PspA protein fragments which contain protection-eliciting epitopes and which are cross-reactive and can be incorporated into a vaccine against disease caused by pneumococcal infection. Modifications are possible within the scope of this invention.

What we claim:

1. An isolated polypentide comprising amino acid residues 1 to 115 of pneumococcal surface protein A (PspA) of Streptococcus pneumoniae.

2. An isolated polypeptide consisting of amino acid residues 1 to 115 of pneumococcal surface protein A (PspA) of Streptococcizs pneumoniae.

3. An isolated polypeptide comprising at least one protection eliciting epitope contained in amino acid residues 1 to 115 of pneumococcal surface protein A (PspA) of Streptococcus pneumoniae.

4. An isolated polypeptide comprising at least one protection eliciting epitope contained in amino acid residues 1 to 155 of pneumococcal surface protein A (PspA) of Streptococcus pneumoniae.

5. An isolated polypeptide comprising amino acid residues 1 to 155 of pneumococcal surface protein A (PspA) of Streptococcus pneumoniae.

6. An isolated polypeptide consisting of amino acid residues 1 to 155 of pneualmococcal surface protein A (PspA) of Streptococcus pneumoniae.

7. A method of eliciting an immunological response in a host susceptible to pneumococcal infection comprising administering the polyoeptide of claim 4.

8. A method of eliciting an immunological response in a host susceptible to pneumococcal infection comprising administering the polypeptide of claim 5.

9. A method of eliciting an immunological response in a host susceptible to pneumococcal infection comprising administering the polypeptide of claim 6.

10. A method of eliciting an immunological response in a host susceptible to pneumococcal infection comprising administering the polypeptide of claim 1.

11. A method of eliciting an immunological response in a host susceptible to pneumococcal infection comprising administering the polypeptide of claim 2.

12. A method of eliciting an immunological response in a host susceptible to pneumococcal, infection comprising administering the polypeptide of claim 3.

13. An immunological composition comprising the polypeptide of any one of claims 1, 2, 3 4, 5, or 6 and a suitable carrier or diluent.

* * * * *

SEQUENCE LISTING (1) GENERAL INFORMATION:

(iii) NUMBER OF SEQUENCES: 20

(2) INFORMATION FOR SEQ ID NO:1:

(i) SEQUENCE CHARACTERISTICS:
      (A) LENGTH: 2085 base pairs
      (B) TYPE: nucleic acid
      (C) STRANDEDNESS: double
      (D) TOPOLOGY: linear (ii) MOLECULE TYPE: protein (iii) HYPOTHETICAL: NO (iv) ANTI-SENSE: NO (vi) ORIGINAL SOURCE:
      (A) ORGANISM: Streptococcus pneumoniae
      (B) STRAIN: Rx1

(vii) IMMEDIATE SOURCE:
      (B) CLONE: JY4313

(ix) FEATURE:
      (A) NAME/KEY: intron
      (B) LOCATION: 1..2085

(ix) FEATURE:
      (A) NAME/KEY: CDS
      (B) LOCATION: join(127..1984)

(xi) SEQUENCE DESCRIPTION: SEQ ID NO:1:

```
AAGCTTATGA TATAGAAATT TGTAACAAAA ATGTAATATA AAACACTTGA CAAATATTTA        60

CGGAGGAGGC TTATACTTAA TATAAGTATA GTCTGAAAAT GACTATCAGA AAAGAGGTAA       120

ATTTAG ATG AAT AAG AAA AAA ATG ATT TTA ACA AGT CTA GCC AGC GTC          168
       Met Asn Lys Lys Lys Met Ile Leu Thr Ser Leu Ala Ser Val
         1               5                  10

CCT ATC TTA GGG GCT GGT TTT GTT GCG TCT CAG CCT ACT GTT GTA AGA         216
Ala Ile Leu Gly Ala Gly Phe Val Ala Ser Gln Pro Thr Val Val Arg
 15                  20                  25                  30

GCA GAA GAA TCT CCC GTA GCC AGT CAG TCT AAA GCT GAG AAA GAC TAT         264
Ala Glu Glu Ser Pro Val Ala Ser Gln Ser Lys Ala Glu Lys Asp Tyr
                 35                  40                  45

GAT GCA GCG AAG AAA GAT GCT AAG AAT GCG AAA AAA GCA GTA GAA GAT         312
Asp Ala Ala Lys Lys Asp Ala Lys Asn Ala Lys Lys Ala Val Glu Asp
                 50                  55                  60

GCT CAA AAG GCT TTA GAT GAT GCA AAA GCT GCT CAG AAA AAA TAT GAC         360
Ala Gln Lys Ala Leu Asp Asp Ala Lys Ala Ala Gln Lys Lys Tyr Asp
         65                  70                  75

GAG GAT CAG AAG AAA ACT GAG GAG AAA GCC GCG CTA GAA AAA GCA GCG         408
Glu Asp Gln Lys Lys Thr Glu Glu Lys Ala Ala Leu Glu Lys Ala Ala
```

-continued

```
           80                    85                    90
TCT GAA GAG ATG GAT AAG GCA GTG GCA GCA GTT CAA CAA GCG TAT CTA          456
Ser Glu Glu Met Asp Lys Ala Val Ala Ala Val Gln Gln Ala Tyr Leu
 95                 100                 105                 110

GCC TAT CAA CAA GCT ACA GAC AAA GCC GCA AAA GAC GCA GCA GAT AAG          504
Ala Tyr Gln Gln Ala Thr Asp Lys Ala Ala Lys Asp Ala Ala Asp Lys
                115                 120                 125

ATG ATA GAT GAA GCT AAG AAA CGC GAA GAA GAG GCA AAA ACT AAA TTT          552
Met Ile Asp Glu Ala Lys Lys Arg Glu Glu Glu Ala Lys Thr Lys Phe
            130                 135                 140

AAT ACT GTT CGA GCA ATG GTA GTT CCT GAG CCA GAG CAG TTG GCT GAG          600
Asn Thr Val Arg Ala Met Val Val Pro Glu Pro Glu Gln Leu Ala Glu
                145                 150                 155

ACT AAG AAA AAA TCA GAA GAA GCT AAA CAA AAA GCA CCA GAA CTT ACT          648
Thr Lys Lys Lys Ser Glu Glu Ala Lys Gln Lys Ala Pro Glu Leu Thr
    160                 165                 170

AAA AAA CTA GAA GAA GCT AAA GCA AAA TTA GAA GAG GCT GAG AAA AAA          696
Lys Lys Leu Glu Glu Ala Lys Ala Lys Leu Glu Glu Ala Glu Lys Lys
175                 180                 185                 190

GCT ACT GAA GCC AAA CAA AAA GTG GAT GCT GAA GAA GTC GCT CCT CAA          744
Ala Thr Glu Ala Lys Gln Lys Val Asp Ala Glu Glu Val Ala Pro Gln
                195                 200                 205

GCT AAA ATC GCT GAA TTG GAA AAT CAA GTT CAT AGA CTA GAA CAA GAG          792
Ala Lys Ile Ala Glu Leu Glu Asn Gln Val His Arg Leu Glu Gln Glu
            210                 215                 220

CTC AAA GAG ATT GAT GAG TCT GAA TCA GAA GAT TAT GCT AAA GAA GGT          840
Leu Lys Glu Ile Asp Glu Ser Glu Ser Glu Asp Tyr Ala Lys Glu Gly
        225                 230                 235

TTC CGT GCT CCT CTT CAA TCT AAA TTG GAT GCC AAA AAA GCT AAA CTA          888
Phe Arg Ala Pro Leu Gln Ser Lys Leu Asp Ala Lys Lys Ala Lys Leu
    240                 245                 250

TCA AAA CTT GAA GAG TTA AGT GAT AAG ATT GAT GAG TTA GAC GCT GAA          936
Ser Lys Leu Glu Glu Leu Ser Asp Lys Ile Asp Glu Leu Asp Ala Glu
255                 260                 265                 270

ATT GCA AAA CTT GAA GAT CAA CTT AAA GCT GCT GAA GAA AAC AAT AAT          984
Ile Ala Lys Leu Glu Asp Gln Leu Lys Ala Ala Glu Glu Asn Asn Asn
                275                 280                 285

GTA GAA GAC TAC TTT AAA GAA GGT TTA GAG AAA ACT ATT GCT GCT AAA         1032
Val Glu Asp Tyr Phe Lys Glu Gly Leu Glu Lys Thr Ile Ala Ala Lys
            290                 295                 300

AAA GCT GAA TTA GAA AAA ACT GAA GCT GAC CTT AAG AAA GCA GTT AAT         1080
Lys Ala Glu Leu Glu Lys Thr Glu Ala Asp Leu Lys Lys Ala Val Asn
        305                 310                 315

GAG CCA GAA AAA CCA GCT CCA GCT CCA GAA ACT CCA GCC CCA GAA GCA         1128
Glu Pro Glu Lys Pro Ala Pro Ala Pro Glu Thr Pro Ala Pro Glu Ala
    320                 325                 330

CCA GCT GAA CAA CCA AAA CCA GCG CCG GCT CCT CAA CCA GCT CCC GCA         1176
Pro Ala Glu Gln Pro Lys Pro Ala Pro Ala Pro Gln Pro Ala Pro Ala
335                 340                 345                 350

CCA AAA CCA GAG AAG CCA GCT GAA CAA CCA AAA CCA GAA AAA ACA GAT         1224
Pro Lys Pro Glu Lys Pro Ala Glu Gln Pro Lys Pro Glu Lys Thr Asp
                355                 360                 365

GAT CAA CAA GCT GAA GAA GAC TAT GCT CGT AGA TCA GAA GAA GAA TAT         1272
Asp Gln Gln Ala Glu Glu Asp Tyr Ala Arg Arg Ser Glu Glu Glu Tyr
            370                 375                 380

AAT CGC TTG ACT CAA CAG CAA CCG CCA AAA GCT GAA AAA CCA GCT CCT         1320
Asn Arg Leu Thr Gln Gln Gln Pro Pro Lys Ala Glu Lys Pro Ala Pro
        385                 390                 395

GCA CCA AAA ACA GGC TGG AAA CAA GAA AAC GGT ATG TGG TAC TTC TAC         1368
Ala Pro Lys Thr Gly Trp Lys Gln Glu Asn Gly Met Trp Tyr Phe Tyr
```

```
                400                 405                 410
AAT ACT GAT GGT TCA ATG GCG ACA GGA TGG CTC CAA AAC AAC GGT TCA    1416
Asn Thr Asp Gly Ser Met Ala Thr Gly Trp Leu Gln Asn Asn Gly Ser
415                 420                 425                 430

TGG TAC TAC CTC AAC AGC AAT GGT GCT ATG GCT ACA GGT TGG CTC CAA    1464
Trp Tyr Tyr Leu Asn Ser Asn Gly Ala Met Ala Thr Gly Trp Leu Gln
                    435                 440                 445

TAC AAT GGT TCA TGG TAT TAC CTC AAC GCT AAC GGC GCT ATG GCA ACA    1512
Tyr Asn Gly Ser Trp Tyr Tyr Leu Asn Ala Asn Gly Ala Met Ala Thr
                450                 455                 460

GGT TGG GCT AAA GTC AAC GGT TCA TGG TAC TAC CTC AAC GCT AAT GGT    1560
Gly Trp Ala Lys Val Asn Gly Ser Trp Tyr Tyr Leu Asn Ala Asn Gly
            465                 470                 475

GCT ATG GCT ACA GGT TGG CTC CAA TAC AAC GGT TCA TGG TAT TAC CTC    1608
Ala Met Ala Thr Gly Trp Leu Gln Tyr Asn Gly Ser Trp Tyr Tyr Leu
        480                 485                 490

AAC GCT AAC GGC GCT ATG GCA ACA GGT TGG GCT AAA GTC AAC GGT TCA    1656
Asn Ala Asn Gly Ala Met Ala Thr Gly Trp Ala Lys Val Asn Gly Ser
495                 500                 505                 510

TGG TAC TAC CTC AAC GCT AAT GGT GCT ATG GCT ACA GGT TGG CTC CAA    1704
Trp Tyr Tyr Leu Asn Ala Asn Gly Ala Met Ala Thr Gly Trp Leu Gln
                    515                 520                 525

TAC AAC GGT TCA TGG TAC TAC CTC AAC GCT AAC GGT GCT ATG GCT ACA    1752
Tyr Asn Gly Ser Trp Tyr Tyr Leu Asn Ala Asn Gly Ala Met Ala Thr
                530                 535                 540

GGT TGG GCT AAA GTC AAC GGT TCA TGG TAC TAC CTC AAC GCT AAT GGT    1800
Gly Trp Ala Lys Val Asn Gly Ser Trp Tyr Tyr Leu Asn Ala Asn Gly
            545                 550                 555

GCT ATG GCA ACA GGT TGG GTG AAA GAT GGA GAT ACC TGG TAC TAT CTT    1848
Ala Met Ala Thr Gly Trp Val Lys Asp Gly Asp Thr Trp Tyr Tyr Leu
        560                 565                 570

GAA GCA TCA GGT GCT ATG AAA GCA AGC CAA TGG TTC AAA GTA TCA GAT    1896
Glu Ala Ser Gly Ala Met Lys Ala Ser Gln Trp Phe Lys Val Ser Asp
575                 580                 585                 590

AAA TGG TAC TAT GTC AAT GGT TTA GGT GCC CTT GCA GTC AAC ACA ACT    1944
Lys Trp Tyr Tyr Val Asn Gly Leu Gly Ala Leu Ala Val Asn Thr Thr
                    595                 600                 605

GTA GAT GGC TAT AAA GTC AAT GCC AAT GGT GAA TGG GTT TAA GCC GAT    1992
Val Asp Gly Tyr Lys Val Asn Ala Asn Gly Glu Trp Val  *
                610                 615

TAA ATT AAA GCA TGT TAA GAA CAT TTG ACA TTT TAA TTT TGA AAC AAA    2040
GAT AAG GTT CGA TTG AAT AGA TTT ATG TTC GTA TTC TTT AGG TAC         2085

(2) INFORMATION FOR SEQ ID NO:2:

(i) SEQUENCE CHARACTERISTICS:
        (A) LENGTH: 619 amino acids
        (B) TYPE: amino acid
        (D) TOPOLOGY: linear (ii) MOLECULE TYPE: protein (xi) SEQUENCE DESCRIPTION: SEQ ID NO:2:

Met Asn Lys Lys Lys Met Ile Leu Thr Ser Leu Ala Ser Val Ala Ile
 1               5                  10                  15

Leu Gly Ala Gly Phe Val Ala Ser Gln Pro Thr Val Val Arg Ala Glu
                20                  25                  30

Glu Ser Pro Val Ala Ser Gln Ser Lys Ala Glu Lys Asp Tyr Asp Ala
            35                  40                  45

Ala Lys Lys Asp Ala Lys Asn Ala Lys Lys Ala Val Glu Asp Ala Gln
        50                  55                  60
```

```
Lys Ala Leu Asp Asp Ala Lys Ala Ala Gln Lys Lys Tyr Asp Glu Asp
 65                  70                  75                  80

Gln Lys Lys Thr Glu Glu Lys Ala Ala Leu Glu Lys Ala Ala Ser Glu
             85                  90                  95

Glu Met Asp Lys Ala Val Ala Ala Val Gln Gln Ala Tyr Leu Ala Tyr
            100                 105                 110

Gln Gln Ala Thr Asp Lys Ala Ala Lys Asp Ala Ala Asp Lys Met Ile
            115                 120                 125

Asp Glu Ala Lys Lys Arg Glu Glu Ala Lys Thr Lys Phe Asn Thr
130                 135                 140

Val Arg Ala Met Val Val Pro Glu Pro Glu Gln Leu Ala Glu Thr Lys
145                 150                 155                 160

Lys Lys Ser Glu Glu Ala Lys Gln Lys Ala Pro Glu Leu Thr Lys Lys
                165                 170                 175

Leu Glu Glu Ala Lys Ala Lys Leu Glu Glu Ala Glu Lys Lys Ala Thr
                180                 185                 190

Glu Ala Lys Gln Lys Val Asp Ala Glu Val Ala Pro Gln Ala Lys
            195                 200                 205

Ile Ala Glu Leu Glu Asn Gln Val His Arg Leu Glu Gln Glu Leu Lys
            210                 215                 220

Glu Ile Asp Glu Ser Glu Ser Glu Asp Tyr Ala Lys Glu Gly Phe Arg
225                 230                 235                 240

Ala Pro Leu Gln Ser Lys Leu Asp Ala Lys Lys Ala Lys Leu Ser Lys
                245                 250                 255

Leu Glu Glu Leu Ser Asp Lys Ile Asp Glu Leu Asp Ala Glu Ile Ala
                260                 265                 270

Lys Leu Glu Asp Gln Leu Lys Ala Ala Glu Glu Asn Asn Asn Val Glu
            275                 280                 285

Asp Tyr Phe Lys Glu Gly Leu Glu Lys Thr Ile Ala Ala Lys Lys Ala
            290                 295                 300

Glu Leu Glu Lys Thr Glu Ala Asp Leu Lys Lys Ala Val Asn Glu Pro
305                 310                 315                 320

Glu Lys Pro Ala Pro Ala Pro Glu Thr Pro Ala Pro Glu Ala Pro Ala
                325                 330                 335

Glu Gln Pro Lys Pro Ala Pro Ala Pro Gln Pro Ala Pro Ala Pro Lys
            340                 345                 350

Pro Glu Lys Pro Ala Glu Gln Pro Lys Pro Glu Lys Thr Asp Asp Gln
            355                 360                 365

Gln Ala Glu Glu Asp Tyr Ala Arg Arg Ser Glu Glu Tyr Asn Arg
370                 375                 380

Leu Thr Gln Gln Gln Pro Pro Lys Ala Glu Lys Pro Ala Pro Ala Pro
385                 390                 395                 400

Lys Thr Gly Trp Lys Gln Glu Asn Gly Met Trp Tyr Phe Tyr Asn Thr
                405                 410                 415

Asp Gly Ser Met Ala Thr Gly Trp Leu Gln Asn Asn Gly Ser Trp Tyr
            420                 425                 430

Tyr Leu Asn Ser Asn Gly Ala Met Ala Thr Gly Trp Leu Gln Tyr Asn
            435                 440                 445

Gly Ser Trp Tyr Tyr Leu Asn Ala Asn Gly Ala Met Ala Thr Gly Trp
            450                 455                 460

Ala Lys Val Asn Gly Ser Trp Tyr Tyr Leu Asn Ala Asn Gly Ala Met
465                 470                 475                 480

Ala Thr Gly Trp Leu Gln Tyr Asn Gly Ser Trp Tyr Tyr Leu Asn Ala
```

```
                        485                 490                 495
Asn Gly Ala Met Ala Thr Gly Trp Ala Lys Val Asn Gly Ser Trp Tyr
                500                 505                 510

Tyr Leu Asn Ala Asn Gly Ala Met Ala Thr Gly Trp Leu Gln Tyr Asn
        515                 520                 525

Gly Ser Trp Tyr Tyr Leu Asn Ala Asn Gly Ala Met Ala Thr Gly Trp
    530                 535                 540

Ala Lys Val Asn Gly Ser Trp Tyr Tyr Leu Asn Ala Asn Gly Ala Met
545                 550                 555                 560

Ala Thr Gly Trp Val Lys Asp Gly Asp Thr Trp Tyr Tyr Leu Glu Ala
                565                 570                 575

Ser Gly Ala Met Lys Ala Ser Gln Trp Phe Lys Val Ser Asp Lys Trp
                580                 585                 590

Tyr Tyr Val Asn Gly Leu Gly Ala Leu Ala Val Asn Thr Thr Val Asp
        595                 600                 605

Gly Tyr Lys Val Asn Ala Asn Gly Glu Trp Val
    610                 615
```

(2) INFORMATION FOR SEQ ID NO:3:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:3:

CCGGATCCAG CTCCTGCACC AAAAAC                                               26

(2) INFORMATION FOR SEQ ID NO:4:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:4:

GCGCGTCGAC GGCTTAAACC CATTCACCAT TGG                                     33

(2) INFORMATION FOR SEQ ID NO:5:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:5:

CCGGATCCTG AGCCAGAGCA GTTGGCTG                                             28

(2) INFORMATION FOR SEQ ID NO:6:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:6:

CCGGATCCGC TCAAAGAGAT TGATGAGTCT G                                         31

(2) INFORMATION FOR SEQ ID NO:7:

```
        (i) SEQUENCE CHARACTERISTICS:
            (A) LENGTH: 31 base pairs
            (B) TYPE: nucleic acid
            (C) STRANDEDNESS: single
            (D) TOPOLOGY: linear (xi) SEQUENCE DESCRIPTION: SEQ ID NO:7:

GCGGATCCCG TAGCCAGTCA GTCTAAAGCT G                                   31

(2) INFORMATION FOR SEQ ID NO:8:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (xi) SEQUENCE DESCRIPTION: SEQ ID NO:8:

CTGAGTCGAC TGGAGTTTCT GGAGCTGGAG C                                   31

(2) INFORMATION FOR SEQ ID NO:9:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (xi) SEQUENCE DESCRIPTION: SEQ ID NO:9:

CCGGATCCAG CTCCAGCTCC AGAAACTCCA G                                   31

(2) INFORMATION FOR SEQ ID NO:10:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (xi) SEQUENCE DESCRIPTION: SEQ ID NO:10:

GCGGATCCTT GACCAATATT TACGGAGGAG GC                                  32

(2) INFORMATION FOR SEQ ID NO:11:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:11:

GTTTTTGGTG CAGGAGCTGG                                                20

(2) INFORMATION FOR SEQ ID NO:12:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (xi) SEQUENCE DESCRIPTION: SEQ ID NO:12:

GCTATGGCTA CAGGTTG                                                   17

(2) INFORMATION FOR SEQ ID NO:13:

(i) SEQUENCE CHARACTERISTICS:
```

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:13:

CCACCTGTAG CCATAGC                                                          17

(2) INFORMATION FOR SEQ ID NO:14:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:14:

CCGGATCCAG CGTCGCTATC TTAGGGGCTG GTT                                        33

(2) INFORMATION FOR SEQ ID NO:15:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:15:

GCAAGCTTAT GATATAGAAA TTTGTAAC                                              28

(2) INFORMATION FOR SEQ ID NO:16:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:16:

GCGCGTCTCT TTGAGCTCTT GTTCTAGTCT                                            30

(2) INFORMATION FOR SEQ ID NO:17:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:17:

CGCGTCGACT CAGAGCTCTT GTTCTAG                                               27

(2) INFORMATION FOR SEQ ID NO:18:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:18:

CGCGTCGACT CACTCATTAA CTGCTTT                                               27

(2) INFORMATION FOR SEQ ID NO:19:

(i) SEQUENCE CHARACTERISTICS:
        (A) LENGTH: 31 base pairs
        (B) TYPE: nucleic acid

```
        (C) STRANDEDNESS: single
        (D) TOPOLOGY: linear (xi) SEQUENCE DESCRIPTION: SEQ ID NO:19:

GCGGATCCCG TAGCCAGTCA GTCTAAAGCT G                              31

(2) INFORMATION FOR SEQ ID NO:20:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:20:

TATTTCAGTT ACGGTTACCA CTTACCCTTA AGGCG                          35
```